United States Patent
Moriyama et al.

(10) Patent No.: US 7,399,273 B2
(45) Date of Patent: Jul. 15, 2008

(54) METHOD FOR HIGH-TEMPERATURE HIGH-PRESSURE STEAM STERILIZATION TREATMENT OF ENDOSCOPE AND ENDOSCOPE

(75) Inventors: Hiroki Moriyama, Akishima (JP); Takehiro Nishiie, Hachioji (JP); Seisuke Takase, Hachioji (JP); Masaaki Miyagi, Hachioji (JP); Atsushi Watanabe, Hino (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/896,791

(22) Filed: Jul. 22, 2004

(65) Prior Publication Data
US 2005/0065402 A1    Mar. 24, 2005

(30) Foreign Application Priority Data
Jul. 22, 2003 (JP) ............................. 2003-200154
Aug. 4, 2003 (JP) ............................. 2003-286093
Dec. 22, 2003 (JP) ............................. 2003-425833

(51) Int. Cl.
*A61B 1/00* (2006.01)

(52) U.S. Cl. .................. 600/133; 600/101; 600/153; 600/158; 600/159

(58) Field of Classification Search ......... 600/101–102, 600/158–159, 153, 133
See application file for complete search history.

(56) References Cited

U.S. PATENT DOCUMENTS

| | | | |
|---|---|---|---|
| 5,156,590 A * | 10/1992 | Vilmar | 604/6.16 |
| 5,288,467 A | 2/1994 | Biermaier | |
| 5,343,854 A * | 9/1994 | Katsurada | 600/146 |
| 5,807,238 A * | 9/1998 | Feldman et al. | 600/133 |
| 5,868,667 A * | 2/1999 | Lin et al. | 600/133 |
| 6,736,772 B2 * | 5/2004 | Ishizuka | 600/133 |
| 2002/0001551 A1 | 1/2002 | Moriyama | |
| 2002/0015673 A1 | 2/2002 | Moriyama | |
| 2002/0072653 A1 | 6/2002 | Ishizuka | |

FOREIGN PATENT DOCUMENTS

| | | |
|---|---|---|
| JP | 4-314439 | 11/1992 |
| JP | 2000-51323 | 2/2000 |
| JP | 2001-190642 | 7/2001 |
| JP | 2002-065577 | 3/2002 |
| JP | 2003-10117 | 1/2003 |

* cited by examiner

*Primary Examiner*—Linda C. M. Dvorak
*Assistant Examiner*—Matthew J. Kasztejna
(74) *Attorney, Agent, or Firm*—Scully, Scott, Murphy & Presser, P.C.

(57) ABSTRACT

A method for autoclave sterilization of an endoscope 2 of the present invention includes the step of making a space, which is defined by the outer side of a channel and an outer covering member of the endoscope 2, communicate with the outside of the endoscope, while at least one end of the channel communicates with the outside of the endoscope 2 and the channel is inserted through the inside 47 of the endoscope. The space 47 and the outside of the endoscope are once brought into the negative pressure. Thereafter, steam is introduced in the space 47 and the outside of the endoscope, and the endoscope 2 is sterilized.

10 Claims, 27 Drawing Sheets

75°C OR MORE

METHOD FOR HIGH-TEMPERATURE HIGH-PRESSURE STEAM STERILIZATION TREATMENT OF ENDOSCOPE AND ENDOSCOPE

This application claims benefit of Japanese Application Nos. 2003-200154 filed on Jul. 22, 2003, 2003-286093 filed on Aug. 4, 2003, and 2003-425833 filed on Dec. 22, 2003, the contents of which are incorporated by this reference.

BACKGROUND OF THE INVENTION

1. Field of the Invention

The present invention relates to a method for a high-temperature high-pressure steam sterilization treatment of an endoscope, wherein the endoscope is subjected to a sterilization treatment with high-temperature high-pressure steam, and an endoscope.

2. Description of the Related Art

In recent years, endoscopes have been used widely in the medical field, wherein endoscopes are inserted into body cavities and the like and, thereby, intracavital deep parts and the like are observed, and if necessary, treatment tools are used, so that medical and therapeutic treatments and the like can be performed.

With respect to medical endoscopes, it is indispensable to reliably disinfect and sterilize endoscopes after using in order to prevent infection and the like.

Recently, in the disinfection and sterilization, autoclave sterilization (high-temperature high-pressure steam sterilization) is becoming the mainstream of the method for sterilizing endoscope apparatuses, wherein no complicated operation attends, it is possible to use immediately after sterilization, and there is an advantage in the running cost.

For example, a method for sterilization treatment to prevent breakage of a covering of an endoscope due to the pressure difference between the inside and the outside of the endoscope during high-temperature high-pressure steam sterilization of the endoscope is disclosed in the conventional art of Japanese Unexamined Patent Application Publication No. 2000-51323.

SUMMARY OF THE INVENTION

A method for autoclave sterilization of an endoscope of the present invention includes the steps of making a space, which is defined by the outer side of a channel and an outer covering member of the endoscope, communicate with the outside of the endoscope while at least one end of the channel communicates with the outside of the endoscope and the channel is inserted through the inside of the endoscope, introducing steam into the space and the outside of the endoscope after the space and the outside of the endoscope are once brought into the negative pressure, and sterilizing the endoscope.

DETAILED DESCRIPTION OF PREFERRED EMBODIMENTS

A plurality of embodiments of the present invention will be described below with reference to the drawings.

First Embodiment

Figure 1:
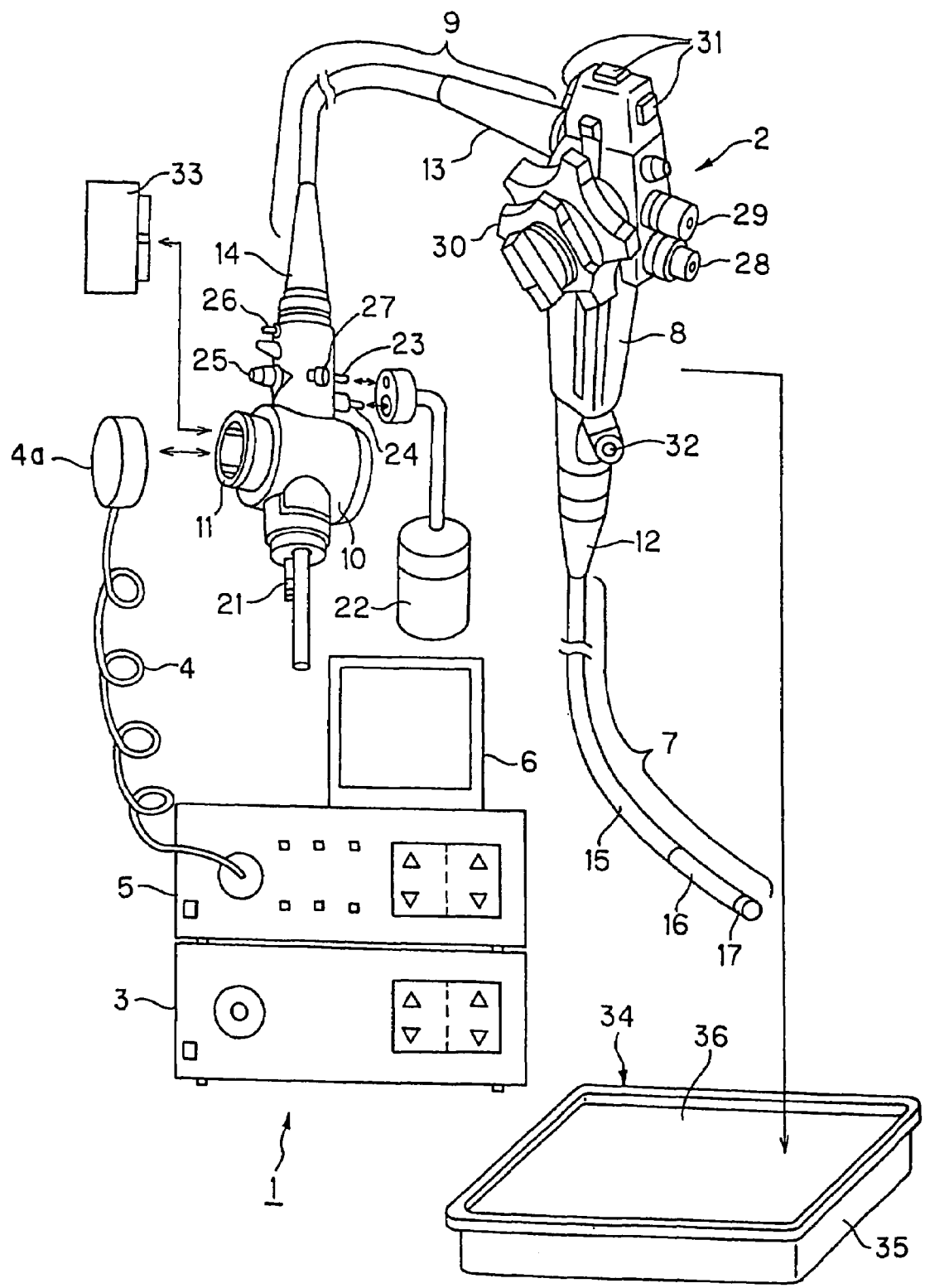
FIG. 1 is an entire configuration diagram of an endoscope apparatus according to a first embodiment of the present invention.
Figure 2:
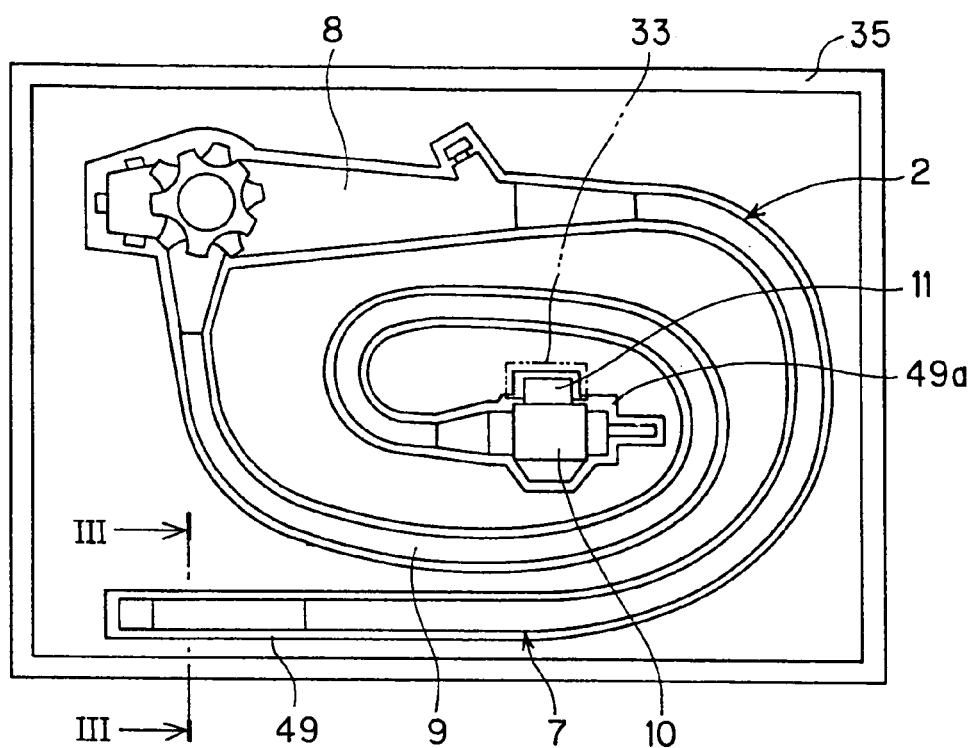
FIG. 2 is a plan view showing the state in which the endoscope according to the first embodiment is stored in a tray.
Figure 3:
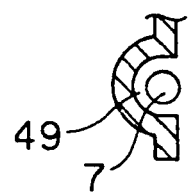
FIG. 3 is a sectional view along a line III-III shown in FIG. 2.
Figure 4:
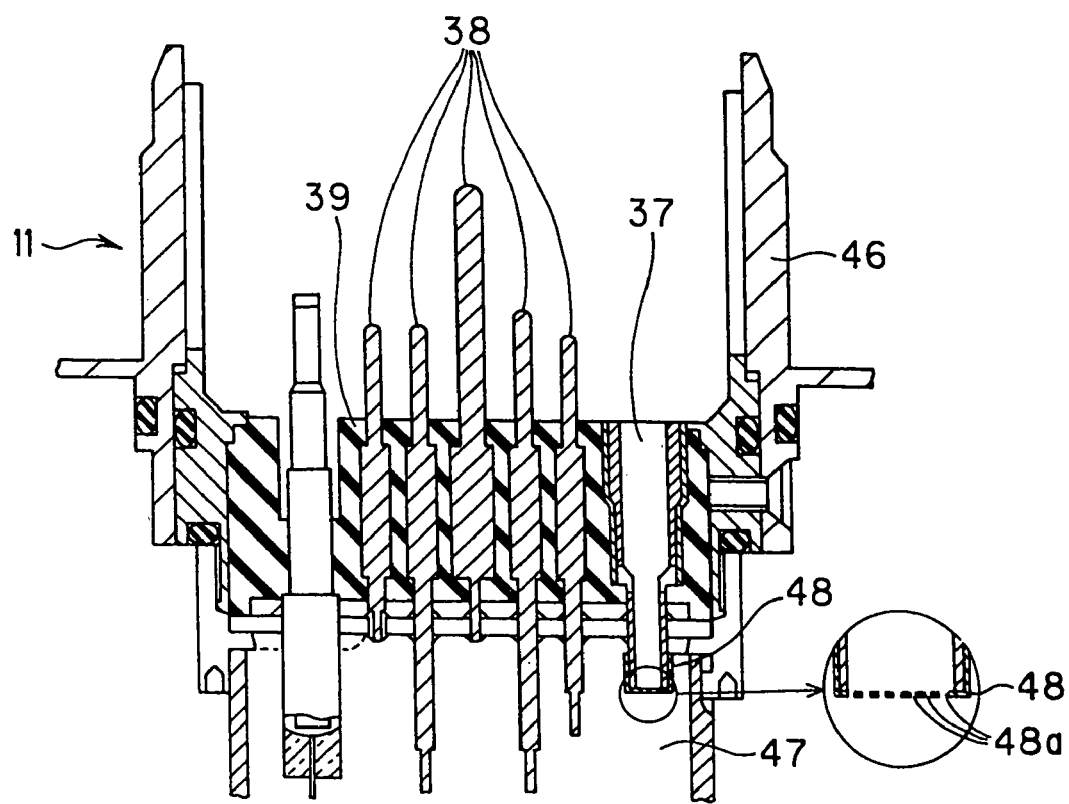
FIG. 4 is a sectional view showing the configuration of an electrical connector portion according to the first embodiment.
Figure 5:
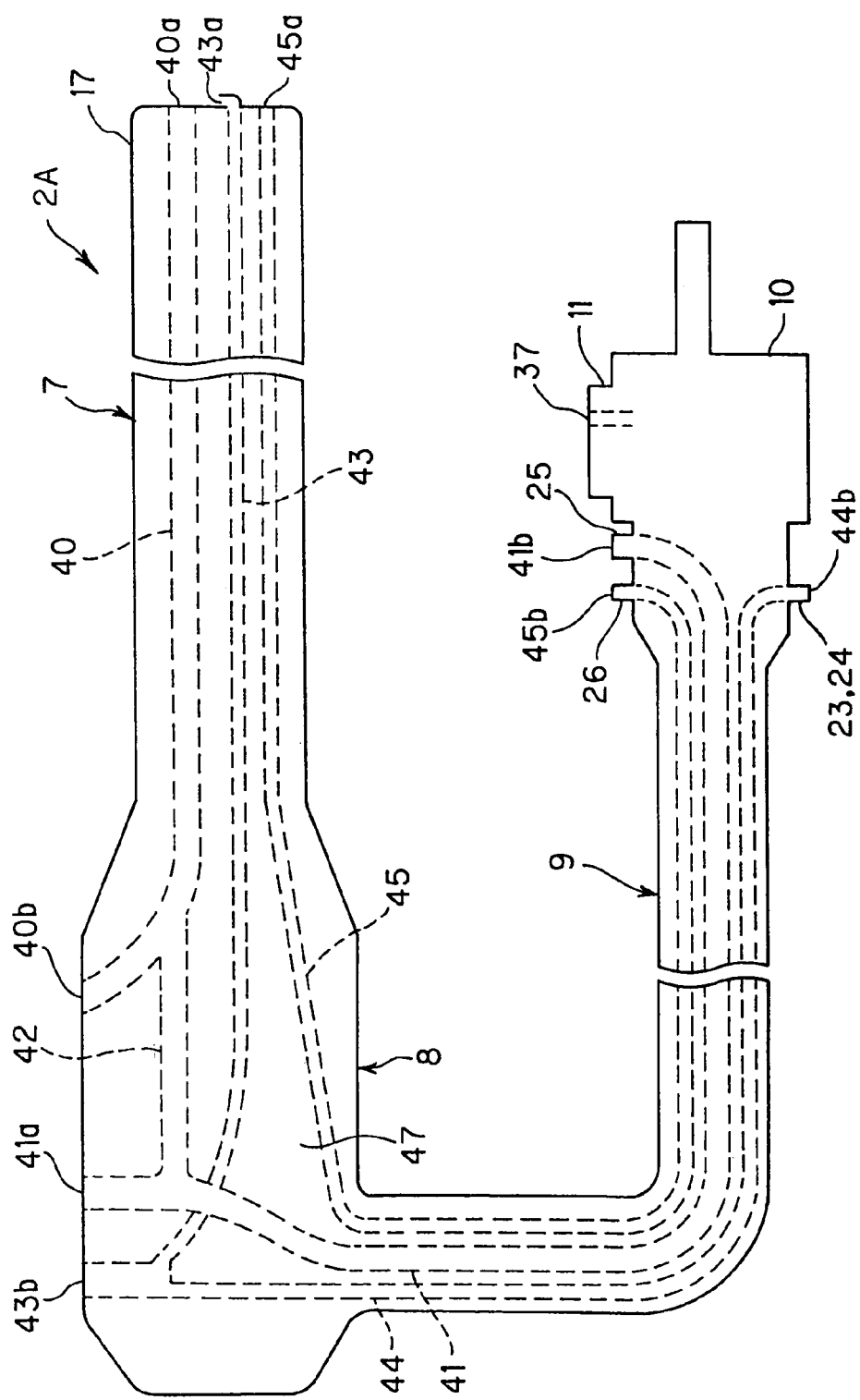
FIG. 5 is a diagram showing a channel system of the endoscope according to the first embodiment.
Figure 6:
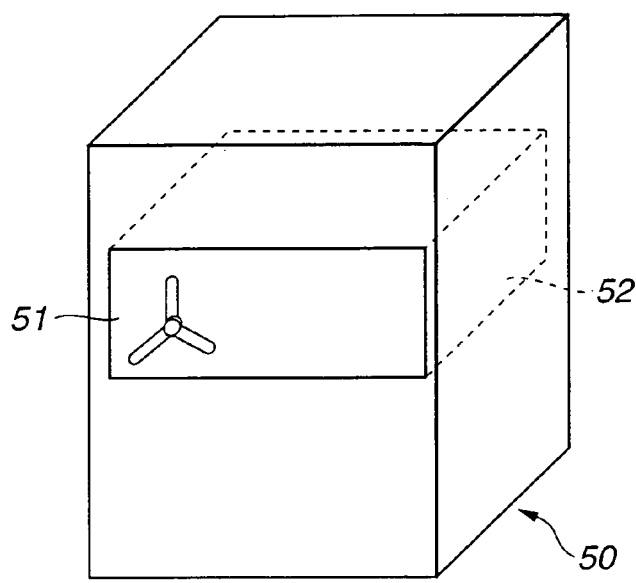
FIG. 6 is a perspective view showing a high-temperature high-pressure steam sterilization apparatus according to the first embodiment.
Figure 7:
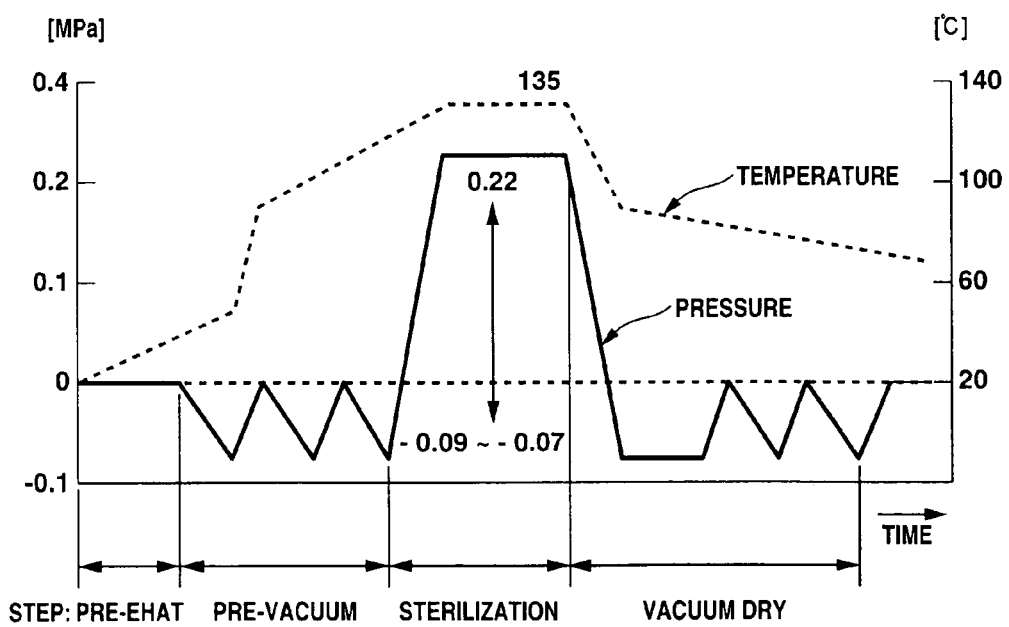
FIG. 7 is a diagram schematically showing a sterilization step with the high-temperature high-pressure steam sterilization apparatus according to the first embodiment.
Figure 8:
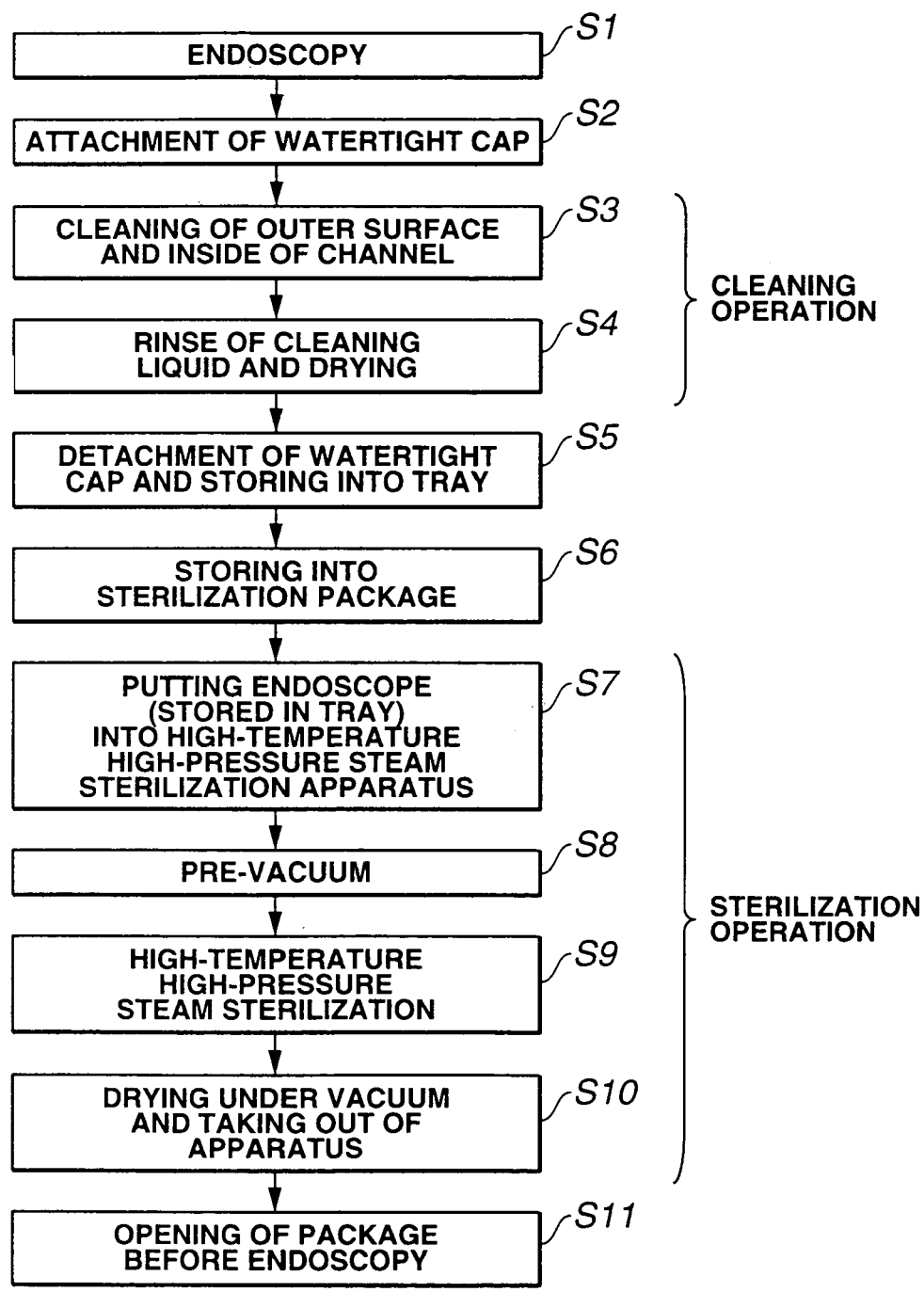
FIG. 8 is a flow chart showing treatment steps of reprocessing after endoscopy, according to the first embodiment.
Figure 9:
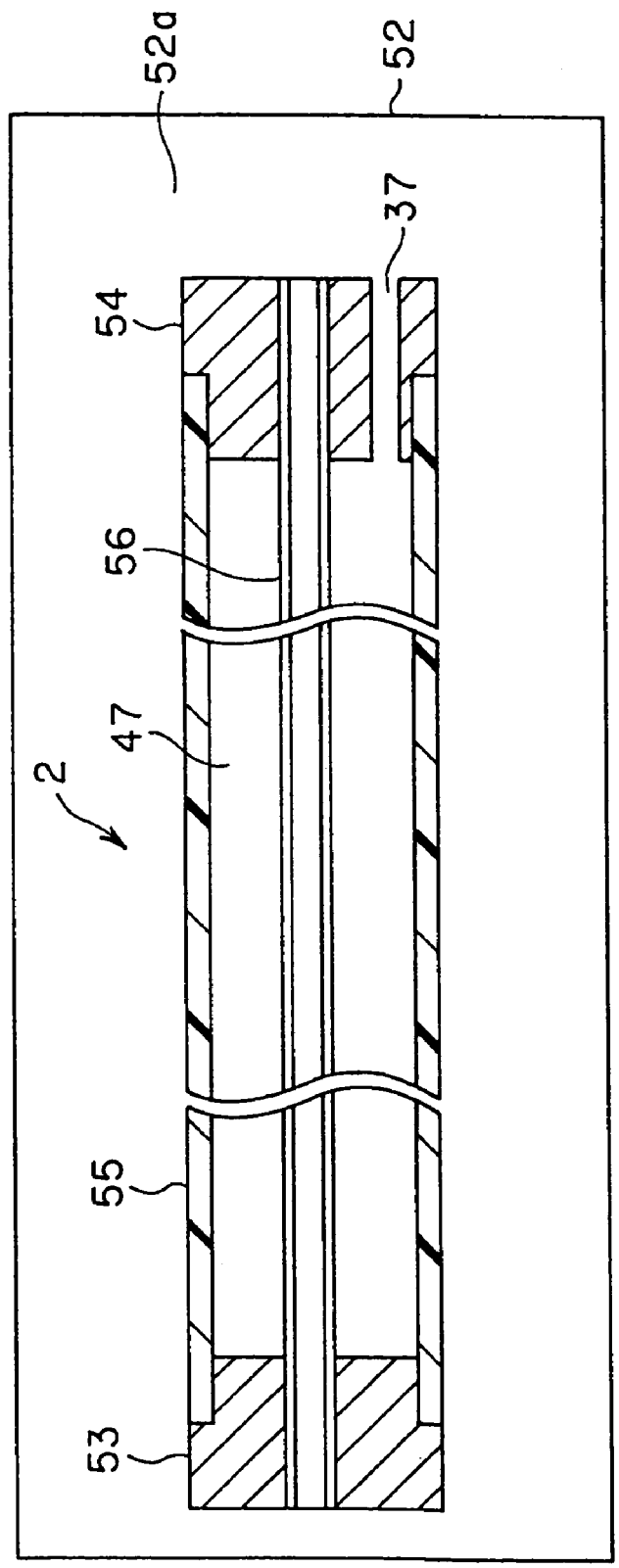
FIG. 9 is a schematic diagram of the endoscope for explaining sterilization operation according to the first embodiment.
Figure 10:
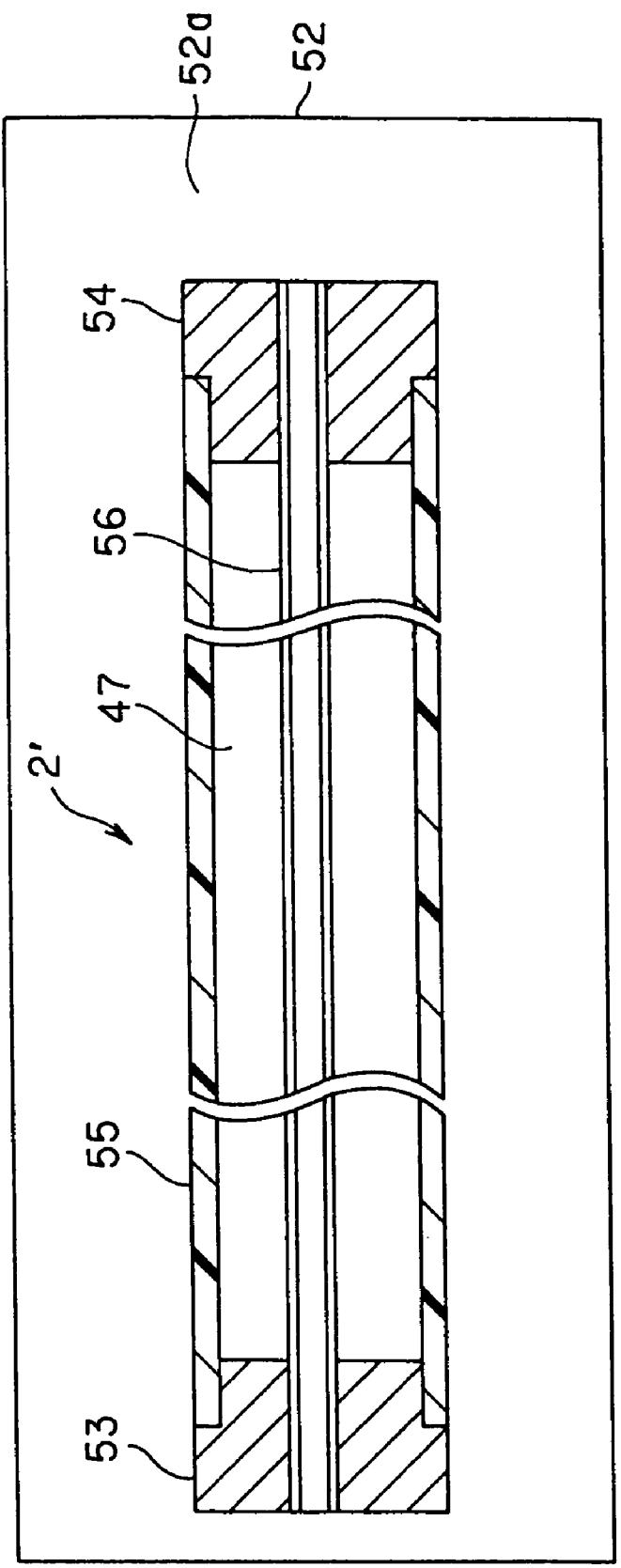
FIG. 10 is a schematic diagram of the endoscope for explaining sterilization operation according to a conventional art.

FIG. 1 to FIG. 8 relate to a first embodiment of the present invention. FIG. 1 is an entire configuration diagram of an endoscope apparatus according to the first embodiment of the present invention. FIG. 2 is a plan view showing the state in which the endoscope according to the first embodiment is stored in a tray. FIG. 3 is a sectional view of a section along a line III-III shown in FIG. 2. FIG. 4 is a sectional view showing the configuration of an electrical connector portion according to the first embodiment. FIG. 5 is a diagram showing a channel system of the endoscope according to the first embodiment. FIG. 6 is a perspective view showing a high-temperature high-pressure steam sterilization apparatus according to the first embodiment. FIG. 7 is a diagram schematically showing a sterilization step with the high-temperature high-pressure steam sterilization apparatus according to the first embodiment. FIG. 8 is a flow chart showing treatment steps of reprocessing after endoscopy, according to the first embodiment. FIG. 9 is a schematic diagram of the endoscope for explaining sterilization operation according to the first embodiment. FIG. 10 is a schematic diagram of the endoscope for explaining sterilization operation according to a conventional art.

As shown in FIG. 1, an endoscope apparatus 1 used for endoscopy is composed of an endoscope 2 provided with image pickup means, a light source unit 3, a video processor 5, and a monitor 6. The light source unit 3 is detachably connected to the endoscope 2, and supplies illumination light to a light guide disposed in the endoscope 2. The video processor 5 is connected to the endoscope 2 via a signal cable 4 to control the image pickup means of the endoscope 2 and, in addition, to process signals obtained from the image pickup means. The monitor 6 displays an image corresponding to an object image output from the processor 5.

The endoscope 2 is cleaned after being used for endoscopy, e.g., observations and treatments, and is composed of members having the resistance against high-temperature high-pressure steam in order that a sterilization treatment can be performed with the high-temperature high-pressure steam after the cleaning is performed. Since the endoscope 2 has a structure in which high-temperature high-pressure steam is intentionally and forcedly flowed into a space portion 47 inside an outer covering member (integument portion) of an insertion portion 7, a control section 8, and the like of the endoscope 2 and, thereby, a sterilization treatment is performed, as described later, it is one of the features that internal signal lines and the like are composed of members having the resistance against the high-temperature high-pressure steam.

The endoscope 2 includes a slender insertion portion 7 which has flexibility and which can be inserted into a body to be examined, more specifically, into body cavities, a control section 8 connected to the proximal end side of the insertion portion 7, a connection cord (universal cord) 9 which has flexibility and which extends from the side portion of the control section 8, a connector portion 10, and an electrical connector portion 11. The connector portion 10 is disposed at the end portion of the connection cord 9, and is detachably connected to the light source unit 3. The electrical connector portion 11 is disposed at the side portion of the connector portion 10. A connector 4a at the end portion of the signal cable 4 is detachably connected to the electrical connector portion 11, wherein the signal cable 4 is detachably connected, to the processor 5 which is an external apparatus.

A vent portion 37, which makes the inside of the endoscope 2 communicate with the outside, is disposed in the electrical connector portion 11, as shown in FIG. 4.

An insertion-portion-side protection boot 12, which serves for preventing tight turning of a joint portion and which is composed of an elastic member, is disposed at the joint portion of the insertion portion 7 and the control section 8. Likewise, a control-section-side protection boot 13 is disposed at the joint portion of the control section 8 and the connection cord 9. Likewise, a connector-portion-side protection boot 14 is disposed at the joint portion of the connection cord 9 and the connector portion 10.

The insertion portion 7 is composed of a flexible tube section 15 having flexibility, a bending section 16 which is disposed in the distal end side of the flexible tube section 15 and which is bendable by the operation of the control section 8, and a distal end portion 17 which is disposed at the distal end and which is provided with an observational optical system, an illuminational optical system, and the like, although not shown in the drawing.

At the distal end portion 17, an air/water supply nozzle for ejecting a cleaning liquid or air toward the optical members on the outer surface of the observational optical system, although not shown in the drawing, through the air supply operation and the water supply operation, and a suction hole which is a distal-end-side opening of a treatment tool channel, although not shown in the drawing, disposed in the insertion portion 7 to insert a treatment tool and to suction a liquid from the body cavity are provided.

Furthermore, a liquid supply hole opened toward an observation object to eject a liquid is disposed at the distal end portion 17.

The connector portion 10 is provided with an air supply base 21 detachably connected to an air supply source, although not shown in the drawing, built in the light source unit 3, and a water supply tank-pressurizing base 23 and a liquid supply base 24, each detachably connected to the water supply tank 22 serving as a liquid supply source. A suction base 25 connected to a suction source, although not shown in the drawing, to perform suction from the aforementioned suction hole is disposed on the back side of the water supply tank-pressurizing base 23 and the liquid supply base 24 of the connector portion 10. An injection base 26 connected to water supply means, although not shown in the drawing, to perform supply of water from the liquid supply hole is disposed in the vicinity of the suction base 25 of the connector portion 10.

Furthermore, an earth terminal base 27 to return a leakage current to a high-frequency treatment apparatus when the high-frequency leakage current is generated in the endoscope during performing of the high-frequency treatment and the like is disposed on the side surface of the connector portion 10.

The control section 8 is provided with an air/water supply operation button 28 for performing an air supply operation or water supply operation, a suction operation button 29 for performing a suction operation, a bending control knob 30 for performing a bending operation of the bending section, a plurality of remote switches 31 for remotely controlling the video processor 5, and a treatment tool insertion hole 32 which is an opening communicating with the treatment tool channel.

A watertight cap 33 is detachably connected to the electric connector portion 11 of the endoscope 2.

The watertight cap 33 is provided with a pressure control valve, although not shown in the drawing.

As shown in FIG. 1, when the endoscope 2 is subjected to the high-temperature high-pressure steam sterilization, a sterilization container case 34 is used.

The container case 34 is open upward, and is composed of a tray 35 serving as an endoscope tray for storing the endoscope 2 to be subjected to the sterilization and a cover member 36 covering the upper side of the tray 35.

The tray 35 and the cover member 36 are provided with a plurality of vent holes, although not shown in the drawing, and steam can pass through the holes. FIG. 2 shows the state in which the endoscope 2 is stored in the tray 35.

As shown in FIG. 2, the tray 35 is provided with an accommodation regulation portion (hereafter referred to as regulation portion) 49, in which concave shave is formed to regulate the storing of the endoscope 2 along the concave shape in a groove portion, that is, in a concave portion, formed corresponding to the shape of the endoscope 2. For example, FIG. 3 shows a section indicated by a line III-III in FIG. 2. The regulation portion 49 is formed into the concave shape of a size slightly larger than the size of each part of the endoscope 2 in order that each part is stored in a predetermined location.

FIG. 4 shows an inside structure of the electrical connector portion 11.

A plurality of contact pins 38 connected to the image pickup signal line and the signal lines of the remote switches 31 are disposed in a insulating support plate 39 attached watertightly to the inner side of a casing 46 of the electrical connector portion 11.

Furthermore, a vent portion 37 serving as a hole or an opening which makes the inside of the endoscope 2 communicate with the outside is provided in the support plate 39 of the electrical connector portion 11 of the endoscope 2 according to the present embodiment. Through the vent portion 37, the outside of the endoscope 2 communicates with the internal space portion 47 enclosed with the integument portion, that is, the outer covering member, of the endoscope 2. Put another way, a communication path communicating with the internal space portion 47 and the outside of the endoscope 2 is formed by the vent portion 37.

A filter 48 provided with a plurality of small holes 48*a* which pass steam but do not pass objects larger than the steam may be disposed in a part of the vent portion 37, as shown in the drawing. That is, the vent portion 37 constituting the communication path is provided with the filter 48 which passes steam but does not pass objects larger than or equal to a predetermined size.

The endoscope 2 according to the present embodiment has a configuration in which when the sterilization treatment is performed with high-temperature high-pressure steam, the high-temperature high-pressure steam is flowed into the space portion 47 from the vent portion 37, the outer side of channels, e.g., the air/water supply channel, communicating with the space portion 47 is heated with the high-temperature high-pressure steam and, thereby, the sterilization treatment can be performed in a short time.

When the watertight cap 33 is attached to the electrical connector portion 11, since the attachment is performed watertightly, any external liquid is not brought into contact with the contact pins 38, nor enter the inside of the endoscope 2 from the vent portion 37.

When the endoscopy is completed, the endoscope 2 is cleaned. At this time, the watertight cap 33 is attached to the electrical connector portion 11 of the endoscope 2 and, thereby, the above-described communication path is blocked. As a result, the cleaning liquid is prevented from entering the inside of the endoscope 2 and being brought into contact with the contact pins 38 so as to deteriorate the surface of the contact pins 38 in the future and, thereby, cause occurrence of failure in current-carrying and the like.

After the cleaning step is completed, the endoscope 2 is stored in the tray 35 while taking a predetermined shape. At this time, a dent 49*a* around the connector portion 10 is a dent along the shape of the connector portion 10, and the connector portion 10 and the electrical connector portion 11 cannot be stored in the dent 82*a* unless the watertight cap 33 is completely detached from the electrical connector portion 11.

FIG. 5 schematically shows various channels built in the inside of the endoscope 2.

A channel 40 is primarily included in the insertion portion 7, and a channel front end 40*a* is opened to the outside at the distal end portion 17. A channel back end 40*b* is opened to the outside at the control section 8. The channel 40 is a channel serving for inserting a treatment tool or for suctioning, for example.

A channel 41 is primarily included in the connection cord 9, a channel front end 41*a* is opened to the outside at the control section 8, and a channel back end 41*b* is opened to the outside at the connector portion 10 through the suction base 25. The channel 41 is a channel serving for suctioning, for example.

A channel 42 is primarily included in the control section 8, the channel front end is shared with the channel back end 40*b*, and is opened to the outside at the control section 8. The channel back end is shared with the channel front end 41*a*, and is opened to the outside at the control section 8. The channel 42 is a channel serving for suctioning, for example.

The channel back end 41*b* (suction base 25) is connected to a channel from a suction device, although not shown in the drawing, and when a suction operation is performed with the suction device while the channel front end 41*a* and the channel back end 40*b* are blocked, suction can be performed from the channel front end 40a through the route of the channel 41, the channel 42, and the channel 40.

A channel 43 is primarily included in the insertion portion 7, a channel front end 43a is opened to the outside at the distal end portion 17, and a channel back end 43b is opened to the outside at the control section 8. The channel 43 is an air/water supply channel serving for supplying air or supplying water in cleaning of a lens surface of the distal end portion 17, for example.

A channel 44 is primarily included in the connection cord 9, the channel front end is shared with the channel back end 43b, and is opened to the outside at the control section 8. A channel back end 44b is opened to the outside at the connector portion 10 through the water supply tank-pressurizing base 23 and the air supply base 24. When the channel back end 43b is blocked and air supply or water supply is performed from the channel back end 44b (the water supply tank-pressurizing base 23, the air supply base 24), air supply or water supply can be performed from the channel front end 43a.

A channel 45 is primarily included in the insertion portion 7 and the connection cord 9, a channel front end 45a is opened to the outside at the distal end portion 17, and a channel back end 45b is opened to the outside at the connector portion 10 through the injection base 26. The channel 45 is a channel serving for supplying water frontward to supply a liquid to an observation object, for example.

As described above, various channels are built in the endoscope 2, while both ends are opened to the outside, and fluids and the like can be inserted through the inside. Furthermore, both the insertion portion 7 and the connection cord 9 are formed from pliable members, and are not solid but hollow. Most of channels in the insertion portion 7 and the connection cord 9 are arranged in a hollow portion while being in an unfixed state in order to meet flexible movement, and the periphery of the channel is substantially space although other built-in members are present.

In the inside of the integument of the endoscope 2, outer sides of these channels in middle portions (here, refers to a location at a distance from the end portion, and refers to a wide range to some extent) of the channels communicate with the surrounding space portion 47, and the space portion 47 communicates with the outside through a vent portion 37. That is, the outer sides of the channels are in the state of communicating with the outside through the vent portion 37 serving as communication means communicating with the space portion 47. Put another way, the space 47 constructed by the outer sides of various channels inserted through the inside of the endoscope 2 and the outer covering member of the endoscope 2 communicates with the outside of the endoscope 2 through the vent portion 37. This communication state through the vent portion 37 can be selected by attachment/non-attachment (detachment) of the watertight cap 33.

In the present embodiment, for example, a space for forming the space portion 47 is ensured in the periphery of the middle portion of the path bonding one opening and another opening of some channel without filling the inside of the integument of the endoscope 2 with fillers and solid matters. Although various built-in members and components are present at some midpoints of the path between the space portion 47 and the vent portion 37, these are arranged in order to avoid interfering the flow of the steam. Therefore, the steam can pass through this path without being hindered.

The endoscope 2 of the present embodiment has a feature that, since the vent portion 37 is disposed and the vent portion 37 can communicate with the space portion 47 in the periphery of each channel disposed in the inside of the endoscope 2 when the sterilization treatment is performed, the space portion 47 can also be adjusted to become in the pre-vacuum state during the pre-vacuum. Consequently, in the following high-temperature high-pressure steam sterilization step, the space portion 47 in the outside of the channel (as well as the inside of the channel) can also be supplied and filled in with high-temperature high-pressure steam, each channel is heated from the outside of the channel and, thereby, the high-temperature high-pressure steam sterilization can be completed in a short time.

The operations in this case will be described later with reference to FIG. 9 and FIG. 10.

FIG. 6 shows a high-temperature high-pressure steam sterilization apparatus 50 in which the endoscope 2 according to the present embodiment is stored in the tray 35, and the high-temperature high-pressure steam sterilization is performed.

The high-temperature high-pressure steam sterilization apparatus 50 is in the shape of a box, and when a door 51 disposed on the front surface is opened, there is a chamber 52 in the inside thereof. The chamber 52 serves as a sterilization chamber in which the high-temperature high-pressure steam sterilization is performed. The tray 35 including the endoscope 2 or the sterilization container case 34 in which the tray 35 is covered with the cover member 36 is put in the chamber 52, the door 51 is closed and, thereafter, the sterilization treatment can be performed.

With respect to the shape of the chamber 52, for example, the size is adjusted to be suitable for tightly storing only one sterilization container case 34 including the endoscope 2.

Means for detecting the relative state between the connector portion 10 (or the electrical connector portion 11) and the watertight cap 33 may be disposed as a part of the high-temperature high-pressure steam sterilization apparatus 50.

For example, some type of chip may be disposed at each of the vicinity of the electrical connector portion 11 and the watertight cap 33 in order that the distance between the two chips is measured with the high-temperature high-pressure steam sterilization apparatus 50 and, thereby, it becomes possible to detect whether the watertight cap 33 is attached to the electrical connector portion 11.

Means for detecting whether the watertight cap 33 is attached to the electrical connector portion 11 by the use of a mechanism other than that described above may be disposed.

Regarding the typical conditions (temperature, time, pressure) of high-temperature high-pressure steam sterilization with the high-temperature high-pressure steam sterilization apparatus 50 or the like, in the US standard ANSI/AAMI ST37-1992 approved by American National Standards Institute and issued by Association for the Advancement of Medical Instrumentation, the sterilization step is specified to be at 132° C. for 4 minutes in pre-vacuum type in which the pressure is reduced before the sterilization step, and the sterilization step is specified to be at 132° C. for 10 minutes in gravity type in which the pressure is not reduced before the sterilization step.

Although the temperature condition during the sterilization step of high-temperature high-pressure steam sterilization varies depending on the format of the high-temperature high-pressure steam sterilization apparatus and the amount of time of the sterilization step, in general, it is set within the range of about 115° C. to 138° C. Some sterilization apparatuses can be set at about 142° C.

The time condition varies depending on the temperature condition during the sterilization step. In general, it is set at about 3 minutes to 60 minutes. Some types of sterilization apparatuses can be set at about 100 minutes.

The pressure in a sterilization chamber during this step is generally set at about +0.2 MPa relative to atmospheric pressure.

In general, a pre-vacuum type high-temperature high-pressure steam sterilization step includes a pre-vacuum step in which the inside of the sterilization chamber storing the target apparatus for sterilization is brought into the state of reduced pressure before a sterilization step and the following sterilization step in which high-temperature high-pressure steam is supplied into the sterilization chamber so as to perform sterilization.

The pre-vacuum step is a step for making steam penetrate into detail of the target apparatus for sterilization during the following sterilization step, and by reducing the pressure in the sterilization chamber, high-pressure high-temperature steam goes throughout the target apparatus for sterilization.

In general, the pressure in the sterilization chamber during the pre-vacuum step is set at about −0.07 MPA to −0.09 MPa relative to atmospheric pressure.

In order to dry the target apparatus for sterilization after sterilization, a drying step may be included, in which the inside of the sterilization chamber is brought into the reduced pressure state again after the sterilization step is completed. In this drying step, the pressure in the sterilization chamber is reduced, the steam is removed from the inside of the sterilization chamber and, therefore, drying of the target apparatus for sterilization in the sterilization chamber is accelerated. In general, the pressure in the sterilization chamber during this drying step is set at about −0.07 to −0.09 MPa relative to atmospheric pressure.

In the present embodiment, the endoscope 2 is subjected to the high-temperature high-pressure steam sterilization while the watertight cap 33 is detached from the electrical connector portion 11, as described later. Since the endoscope 2 is provided with the vent portion 37, as described above, the high-temperature high-pressure steam sterilization treatment can be completed in a short time.

A method for high-temperature high-pressure steam sterilization of the endoscope 2, according to the present embodiment, will be described below. FIG. 7 shows an example of entire steps in the high-temperature high-pressure steam sterilization of the endoscope 2 by the use of the high-temperature high-pressure steam sterilization apparatus 50.

As shown in FIG. 7, the entire steps are composed of a pre-heat step, a pre-vacuum step, a sterilization step, and a vacuum dry step. In FIG. 7, a solid line indicates the state of pressure, and a dotted line indicates the state of temperature. With respect to the pressure, the state of atmospheric pressure is taken as 0. When a pressure is applied, the pressure is indicated by a positive value, and when a vacuum is produced, the pressure is indicated by a negative value.

In FIG. 7, the pre-vacuum is performed three times at −0.09 to −0.07 MPA of vacuum. During this time, steam is supplied, and the temperature is raised (schematically indicated by a rough line in FIG. 7).

In the sterilization step, the pressure is adjusted at 0.22 MPA, and the sterilization is performed at a temperature of 135° C. (the temperature and the pressure are in correspondence with each other).

FIG. 8 shows steps of reprocessing, wherein after the endoscopy with the endoscope 2 is completed, a cleaning operation and a sterilization operation are performed in order that the endoscopy can be performed again.

As shown in FIG. 8, the endoscopy is performed in step S1, and after the endoscopy is completed, as shown in step S2, the watertight cap 33 is attached to the electrical connector portion 11 to make the electrical connector portion 11 waterproof, so that the watertightness of the endoscope 2 is ensured.

Subsequently, a cleaning operation (cleaning step) composed of step S3 and step S4 is performed. In step S3, the endoscope 2 in the watertight state is inserted in a cleaning tank or the like, so that the outer surface of the endoscope 2 and inside of the channels are cleaned.

Thereafter, as shown in step S4, a rinse of a cleaning liquid and drying are performed, so that the cleaning operation is completed.

After this cleaning operation is completed, as shown in step S5, the watertight cap 33 is detached from the electrical connector portion 11, and the endoscope 2 is stored in the tray 35.

When the endoscope 2 is stored in the tray 35, if the watertight cap 33 is not detached, the connector 10 cannot be stored in the regulation portion 49a of the tray 35. Consequently, the user can recognize that the endoscope 2 with the watertight cap 33 being not detached is in the state unsuitable for going to the next step. With respect to this situation, in FIG. 2, the state in which the watertight cap 33 is attached is indicated by a chain double-dashed line.

Furthermore, even if the user attempts to forcedly put the sterilization container case 34 into the high-temperature high-pressure steam sterilization apparatus 50 in spite of the fact that the connector 10 is not stored in the tray 35, since the storing shape of the chamber 52 is adjusted to be a shape suitable for tightly storing only one sterilization container case 34 including the endoscope 2, it is impossible to put the case 34 into the chamber 52 when the connector 10 is not stored and is floated and, thereby, the user can also recognize that it is impossible to proceed to the sterilization operation.

As in the above description, the high-temperature high-pressure steam sterilization apparatus 50 may detect whether the watertight cap 33 is attached to the electrical connector portion 11 by the use of detection means.

The endoscope 2 is thus stored in the tray 35 of the sterilization container case 34, and is covered with the cover member 36. Subsequently, as shown in S6, the sterilization container case 34 including the endoscope 2 is stored, or packed, in a sterilization package, e.g., a peel package. The packing in the sterilization package is reliably performed in order that bacteria in outside air cannot enter (air and steam pass through but bacteria cannot enter).

The sterilization operation (sterilization step) from step S7 to step S10 is performed. In step 7, the endoscope 2 in the state of being stored in the tray 35 (or the sterilization container case 34) is put into the high-temperature high-pressure steam sterilization apparatus 50.

In the following sterilization operation, the space of the chamber 52 communicates with the inside of the endoscope 2 (the space portion 47 in the periphery of the middle portion of the above-described channels to be more precise) through the vent portion 37.

With respect to the high-temperature high-pressure steam sterilization apparatus 50, a pre-heat and pre-vacuum step (vacuum step) in step S8 is performed before proceeding to a high-temperature high-pressure steam sterilization step in step S9.

In particular, during the pre-vacuum step, the inside of the chamber 52 and the space portion 47 in the endoscope 2 are brought into a vacuum state, and then the pressure is returned to an original pressure while steam is supplied. This process is performed at least once.

It is desirable that the pre-vacuum step is performed plural times because air is adequately removed from the chamber 52 and the space portion 47 in the endoscope 2 and, thereby, steam readily substitutes for the air in the chamber 52 and the space portion 47 in the endoscope 2 during the high-temperature high-pressure steam sterilization step in the following step S9.

The high-temperature high-pressure steam sterilization in step S9 is performed after this pre-vacuum step.

The endoscope 2 can be sterilized with high-temperature high-pressure steam through this high-temperature high-pressure steam sterilization.

After this high-temperature high-pressure steam sterilization, the vacuum dry step (step of drying under vacuum), as shown in step S10, is performed.

By performing the step of drying under vacuum, steam entered in the space portion 47 of the endoscope 2 can be discharged and removed through the vent portion 37 to the outside, the inside of the endoscope 2 is not brought into the state of being wet with water, and the durability of constituents in the endoscope 2 can be maintained. That is, the deterioration due to rust and moisture can be minimized. Consequently, it is desirable that the drying is performed under vacuum.

After this drying step is performed, the endoscope 2 covered with the sterilization package is taken out of the high-temperature high-pressure steam sterilization apparatus 50.

As shown in step 11, the sterilization package is opened before performing endoscopy, and the endoscope 2 sterilized and stored in the sterilization container case 34 is taken out. Subsequently, the endoscope 2 can be used for the endoscopy.

The operation and advantage of disposition of the vent portion 37 will be described below with reference to FIG. 9 and FIG. 10. FIG. 9 schematically shows the case where the endoscope 2 provided with the vent portion 37 is stored in the chamber 52 in the present embodiment. For purposes of comparison, the case where the endoscope 2' not provided with the vent portion 37 is stored in the chamber 52 is shown in FIG. 10. Practically, the endoscopes 2 and 2' are stored in the sterilization container case 34 and, furthermore, are covered with sterilization packages which pass steam. However, the packages are not shown in FIG. 9 and FIG. 10 for the sake of simplification.

In the endoscope 2 shown in FIG. 9, the space portion 47 in the inside of the endoscope 2 communicates with a space portion 52a in the chamber 52 through the vent portion 37. On the other hand, in the endoscope 2' shown in FIG. 10, the vent portion 37 is not disposed and, therefore, the space portion 47 in the inside of the endoscope 2' is cut off from the space portion 52a in the chamber 52.

In FIG. 9 and FIG. 10, the endoscope 2 is composed of end portions 53 and 54, an integument tube 55 fixed thereto, a channel 56 (for example, a simulation of the channel 45), both ends of which are opened at the end portions 53 and 54 and which is stored in the integument tube 55, and the space portion 47. In FIG. 9, the vent portion 37 is disposed in the end portion 54.

In the case shown in FIG. 10, since the space portion 47 becomes an enclosed space cut off from the space portion 52a of the chamber 52, even when the space portion 52a of the chamber 52 is filled in with high-temperature high-pressure steam during the high-temperature high-pressure sterilization step, the pressure in the space portion 47 is not increased, and the temperature is resistant to rising as well.

Consequently, even when steam enters into the channel 56 after the pre-vacuum step, the temperature of the steam becomes resistant to rising as the steam goes into the deep of the channel 56, that is, as the steam goes to the location farther from the end portion 54. This is because the temperature is readily lowered by the space portion 47 midway through the channel 56. Therefore, it may take a significantly long time to reliably perform sterilization.

Generally in many cases, endoscopy is performed plural times in the same day and, in many cases, the endoscope used in the first inspection is reprocessed and used on several occasions in the same day. At that time, it is desired that the reprocessing can be performed promptly and reliably as much as possible.

The endoscope 2 according to the present embodiment is brought into the state shown in FIG. 9. Since the vent portion 37 is disposed, steam enters from the vent portion 37 into the space portion 47 during the steam supply after the pre-vacuum.

Therefore, with respect to the space portion 52a in the chamber 52 and the space portion 47, the pressures readily become substantially equal, and substantially equivalent steam presents. Consequently, even a deep position of the channel 56 is applied with a similar level of heat from the outside of the channel 56 by the high-temperature high-pressure steam filled in the space portion 52a of the chamber 52 as well as from the inside of the channel 56, so that every position in the channel 56 can be sterilized promptly.

One important factor of the vent portion 37 is the size thereof.

The vent portion 37 is assumed to be very small or to have a small diameter (for example, 0.1 mm) relative to the volume of the space portion 47.

As a result, the space portion 47 cannot synchronize to the speed of the pressure change in the chamber 52, and a time lag occurs.

In the pre-vacuum step, for example, even when the state of −0.08 MPA is repeated 3 times in the chamber 52, the pressure increase due to high-temperature high-pressure steam may start in the chamber 52 before the inside of the space portion 47 reaches −0.08 MPA, for example, when the inside of the space portion 47 reaches about 0.03 MPA.

Consequently, since the inside of the space portion 47 is not completely subjected to prevacuum, the air originally present in the space portion 47 remains significantly, and the substitution of steam may become inadequate. At this time, if the inside of the chamber 52 is kept at a minimum pressure for longer time, the pressure in the space portion 47 becomes a similar pressure in the end. However, the increase in time is a direction opposite to the state required by the user.

In the sterilization step with the high-temperature high-pressure steam as well, even when the inside of the chamber 52 reaches 0.22 MPA, the space portion 47 takes a long time to reach and, therefore, delays. As a result, the sterilization time (maximum temperature state) must be extended in order to achieve sterilization. This is a direction opposite to the state required by the user as well.

In this manner, it is desirable that the size of the vent portion 37 is an appropriate size relative to the volume of the space portion 47.

The larger size, for example, of 1 mm or more, if possible, of 5 mm or more, or of 10 mm or more, is more desirable. If possible, the area of the vent portion 37 is larger than the area of clearance of the portion having a minimum clearance among the space portion 47 in the inside of the endoscope 2, communicating with the vent portion 37, because the vent portion 37 can be prevented from becoming a bottleneck in entrance of the steam.

As described above, in the present embodiment, the volume of the inside space of the endoscope 2 and the size of the vent portion 37 are adjusted in order that the step progresses while the pressures in the chamber 52 and the space portion 47 in the endoscope 2 are always substantially equal during the pre-vacuum step and the high-temperature high-pressure steam sterilization step. Consequently, the sterilization treatment in the channel can be reliably performed in a short time.

When the filter 48 which passes steam but does not pass objects having some extent of size is disposed in a part of the vent portion 37, as shown in FIG. 4, a lubricant and the like used in the endoscope 2 can be prevented from flowing to the outside in the event of the sterilization operation being performed in the state in which the watertight cap 33 is detached. A filter provided with a plurality of holes which are small to such an extent that only steam is passed may be attached.

As described above, according to the first embodiment, when the high-temperature high-pressure steam sterilization of the endoscope is performed, sterilization in channels built in the endoscope can be performed more promptly and reliably. The sterilization treatment in the channels and the like can be performed in a short time with a simple configuration.

Second Embodiment

A second embodiment of the present invention will be described below with reference to FIG. 11. In the description of the first embodiment, the electrical connector portion 11 is provided with the vent portion 37. The present embodiment is a modification in which the vent portion 37 is disposed in a portion other than the electrical connector portion 11. The same constituents as that in the first embodiment are indicated by the same reference numerals as in the first embodiment and explanations thereof will not be provided.

The points which should be improved in the case where the vent portion 37 is disposed in the electrical connector portion 11 are listed below.

(a) Since the electrical connector portion 11 (or the connector portion 10) is a portion in contact with the light source unit 3 and the processor 5, the electrical connector portion 11 is located at the farthest position from the insertion portion 7. Therefore, if the vent portion 37 is not adequately large, steam is resistant to reaching the channel built in the insertion portion 7 through the vent portion 37.

(b) As described in the first embodiment, it is desirable that the vent portion 37 is as large as possible. However, in the case where the endoscope 2 and a conventional endoscope which cannot be subjected to high-temperature high-pressure steam sterilization are made possible to commonly connect to the light source unit 3 and the processor 5 (to ensure compatibility), the electrical connector portion 11 of the endoscope 2 cannot be made larger than that in the conventional endoscope. The vent portion 37 needs to be disposed in such a limited space and, therefore, the vent portion 37 tends to have relatively small size.

(c) The space portion 47 immediately inside the contact pins 38 shown in FIG. 4 includes many convoluted wirings. In some cases, the wirings may hinder the entrance of steam from the vent portion 37. Those wirings are bundled into one or several cables at a location a short distance from the electrical connector portion 11.

Figure 11:
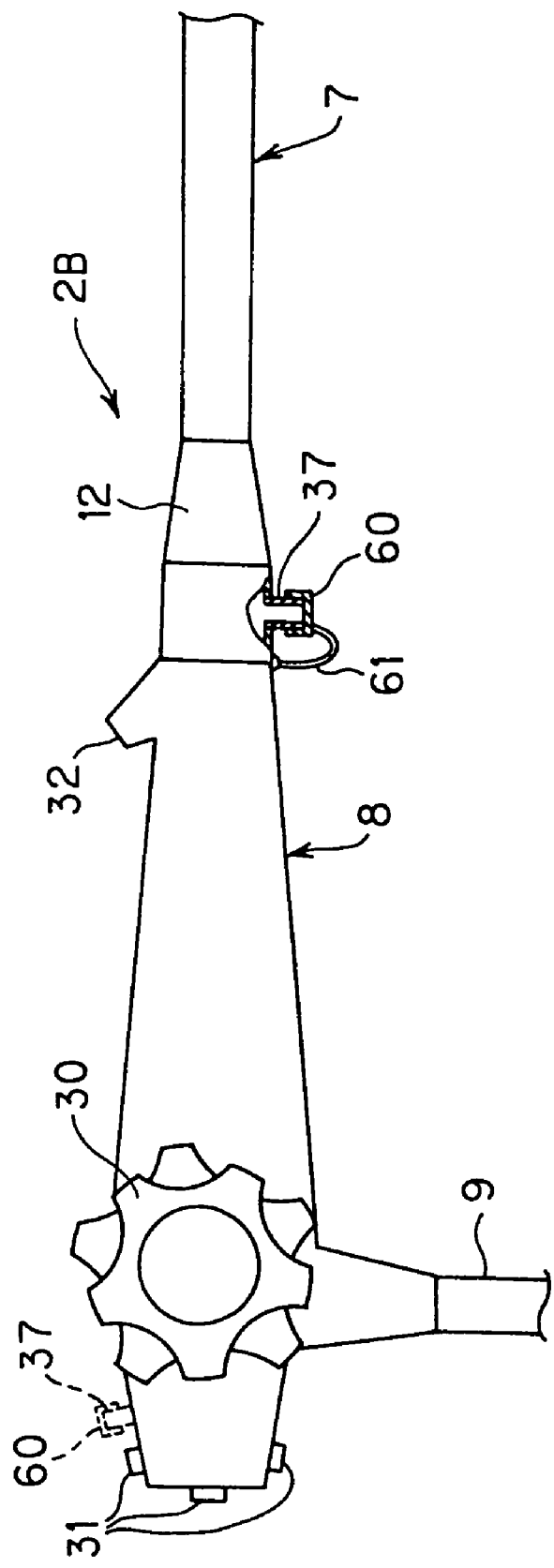
FIG. 11 is a plan view showing an endoscope according to a second embodiment of the present invention.

In consideration of these points, with respect to an endoscope 2B shown in FIG. 11, the vent portion 37 communicating with the space portion 47 in the endoscope 2B is disposed in a part of the control section 8. In this case, a watertight cap 60 is freely detachably attached to the vent portion 37, and the watertight cap 60 is connected to the control section 8 with a string member 61.

These vent portion 37 and watertight cap 60 may be disposed in the vicinity of the back end of the control section 8, as indicated by broken lines.

The tray 35 is made to have a shape in which the endoscope 2B cannot be stored in the sterilization container case 34 unless the watertight cap 60, which is attached to the vent portion 37 during inspection and cleaning, is detached, in the case where the endoscope 2B shown in FIG. 11 is stored in the sterilization container case 34.

Means which notifies the user of the communication state of the vent portion 37 with the outside may be disposed.

According to the present embodiment, the vent portion 37 is disposed in the control section 8 and, thereby, is formed at the location in the vicinity of the insertion portion 7, so that the steam entered from the vent portion 37 is readily made to go throughout the space portion 47 in the endoscope 2.

The watertight cap 60 is connected with a string member 61 and, thereby, the watertight cap 60 is prevented from being lost.

Figure 12:
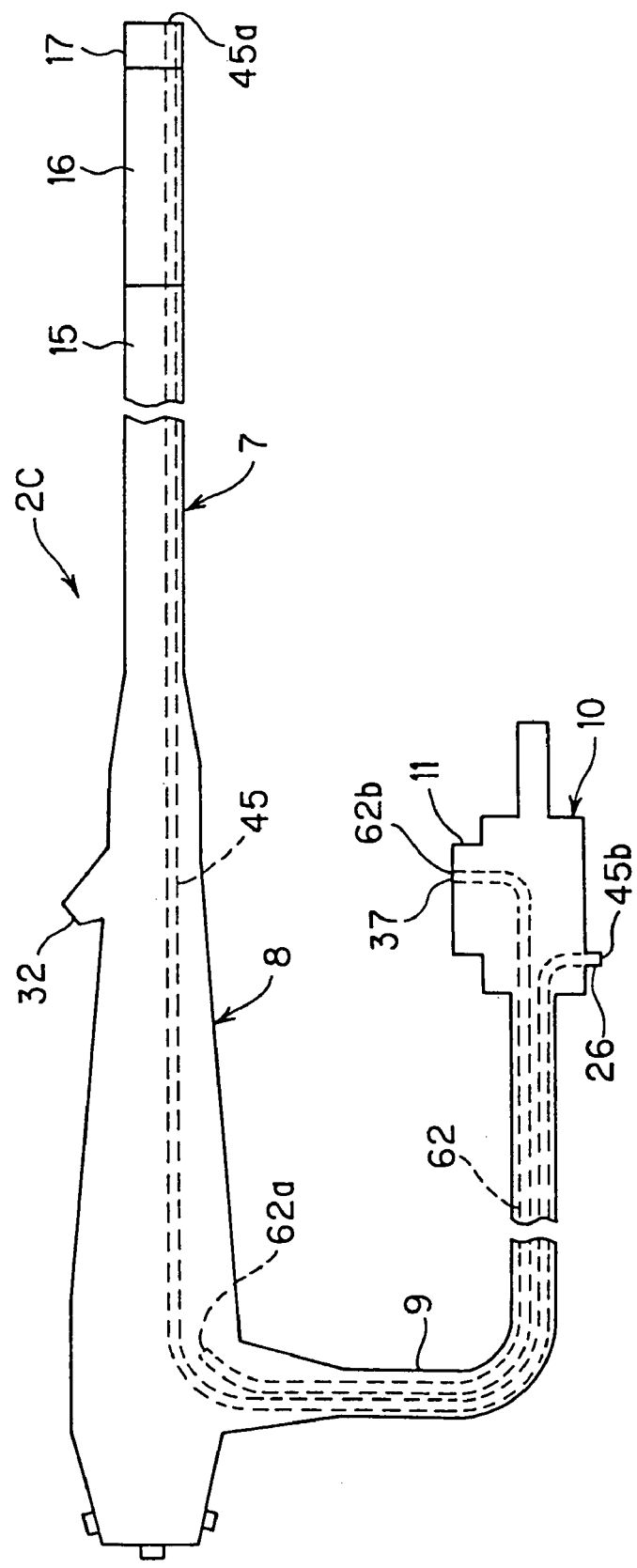
FIG. 12 is a plan view schematically showing a first modification of the endoscope shown in FIG. 11.

With respect to an endoscope 2C shown in FIG. 12, which is a modification of the present embodiment, the vent portion 37 is disposed in the electrical connector portion 11 as in the first embodiment.

In this case, if no modification is made, the above-described points (a) and (b), which should be improved, still remain. However, the points are almost overcome by connecting one end 62b of a tube 62 to the vent portion 37 and making the other end portion 62a communicate with the space portion 47 in the inside of the control section 8 while the tube 62 is inserted through the connection cord 9. That is, the tube 62, which is a channel member connecting the end portion 62b opened to the outside of the endoscope and the end portion 62a disposed at a predetermined location in the inside of the endoscope, is provided as a communication path.

That is, a steam entrance path is formed by the tube 62, steam is allowed to readily enter the control section 8 and connection cord 9 side apart from the insertion portion 7 of the endoscope 2C by the tube 62, and connection to the common light source unit 3 and processor 5 can be performed as in the conventional endoscope.

According to the present modification, the weight of the control section 8 is not increased in contrast to that in the case where the vent portion 37 is disposed in the control section 8, and the operability similar to that in the conventional endoscope can be ensured.

In another modification, the vent portion 37 may be disposed not in the electrical connector portion 11 but in the connector portion 10, at the location in the side nearer to the control section 8 than is the electrical connector portion 11, for example, in the vicinity of the suction base 25 or the injection base 26.

In this manner, it is also possible to make the vent portion 37 relatively large, and the points (b) and (c) can be overcome.

Figure 13:
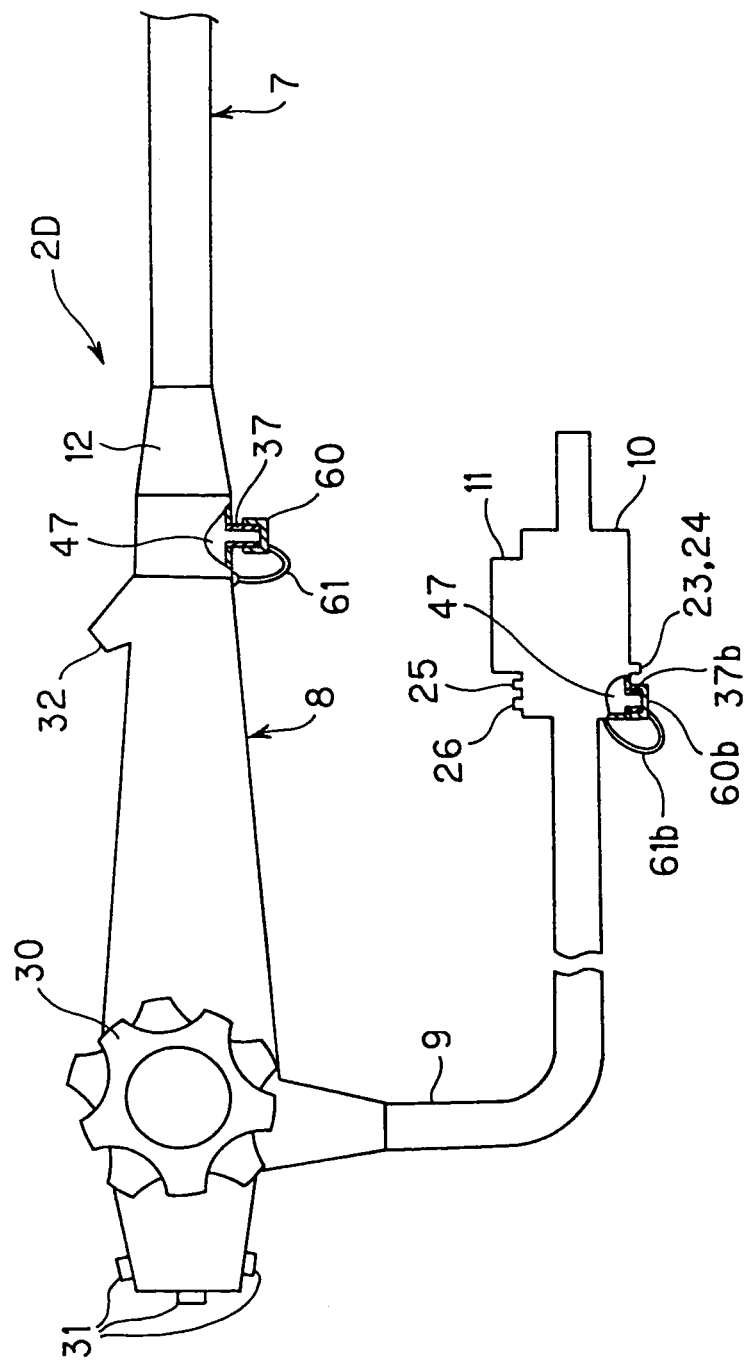
FIG. 13 is a plan view showing a second modification of the endoscope shown in FIG. 11.

In another modification, vent portions may be disposed in a plurality of locations. FIG. 13 shows an endoscope 2D in this case.

In the endoscope 2D, the vent portion 37 is disposed in the control section 8 in order that the vent portion 37 can be covered with the watertight cap 60, as shown in FIG. 11, and in addition, a vent portion 37b is disposed in the portion other than the electrical connector portion 11 in the connector portion 10, for example, in the vicinity of the suction base 25 or the injection base 26. The vent portion 37b can also be made waterproof by, for example, a watertight cap 61b connected to a string member 61b.

As described above, the vent portion 37 and vent portion 37b may be disposed at a plurality of locations, for example, a plurality of locations apart from each other, in one endoscope 2D.

In this manner, the slender channels in the slender endoscope 2D can be sterilized in a short time through sterilization by the steam from the vent portions 37 and 37b at a plurality of locations outside the channel as well as from the inside of the channel, wherein a high temperature state is set in a short time.

As described above, according to the second embodiment, when the high-temperature high-pressure steam sterilization of the endoscope is performed, sterilization in channels built in the endoscope can be performed more promptly and reliably.

(Third Embodiment)

Figure 14:
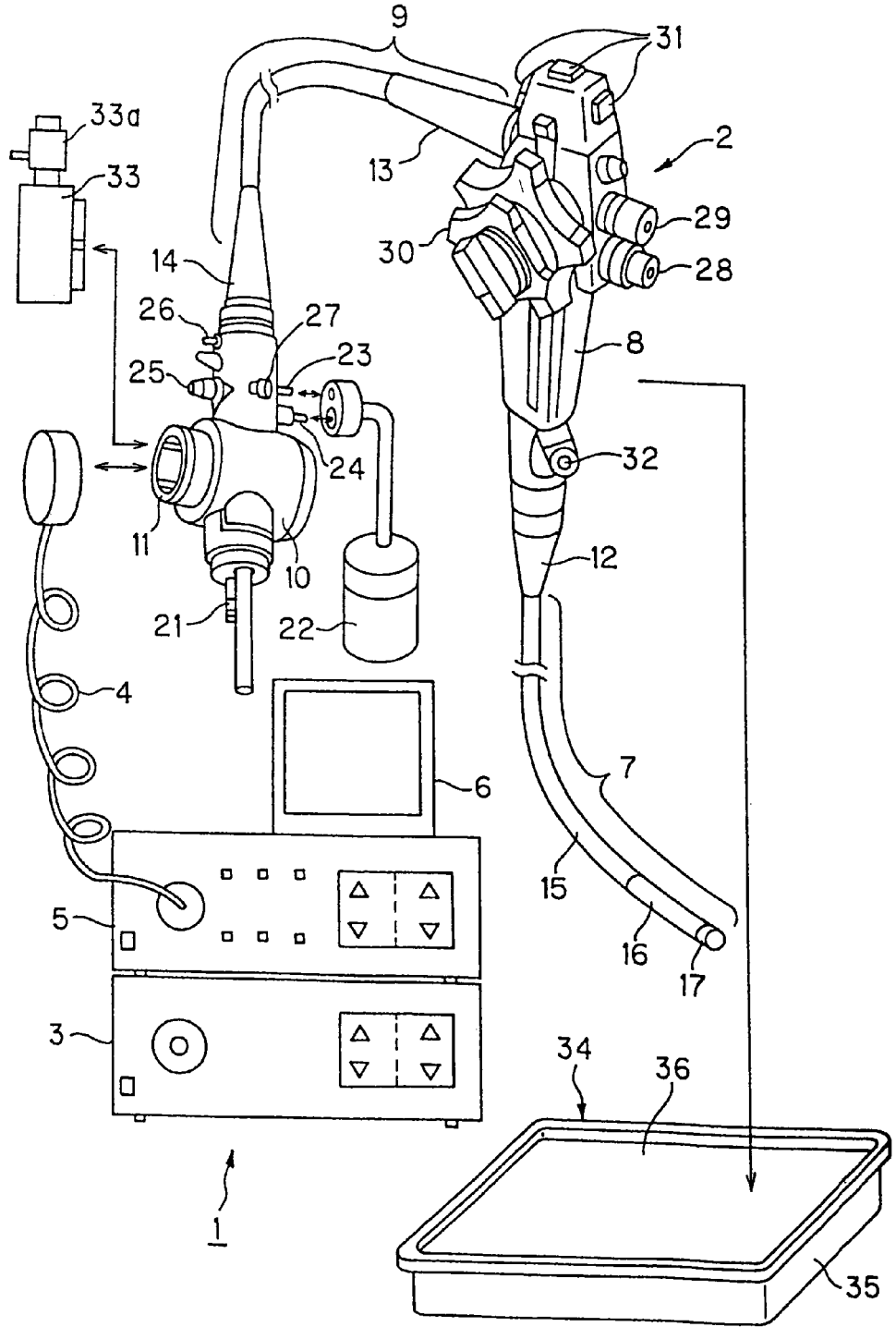
FIG. 14 is an entire configuration diagram of an endoscope apparatus provided with an endoscope according to a third embodiment of the present invention.
Figure 15:
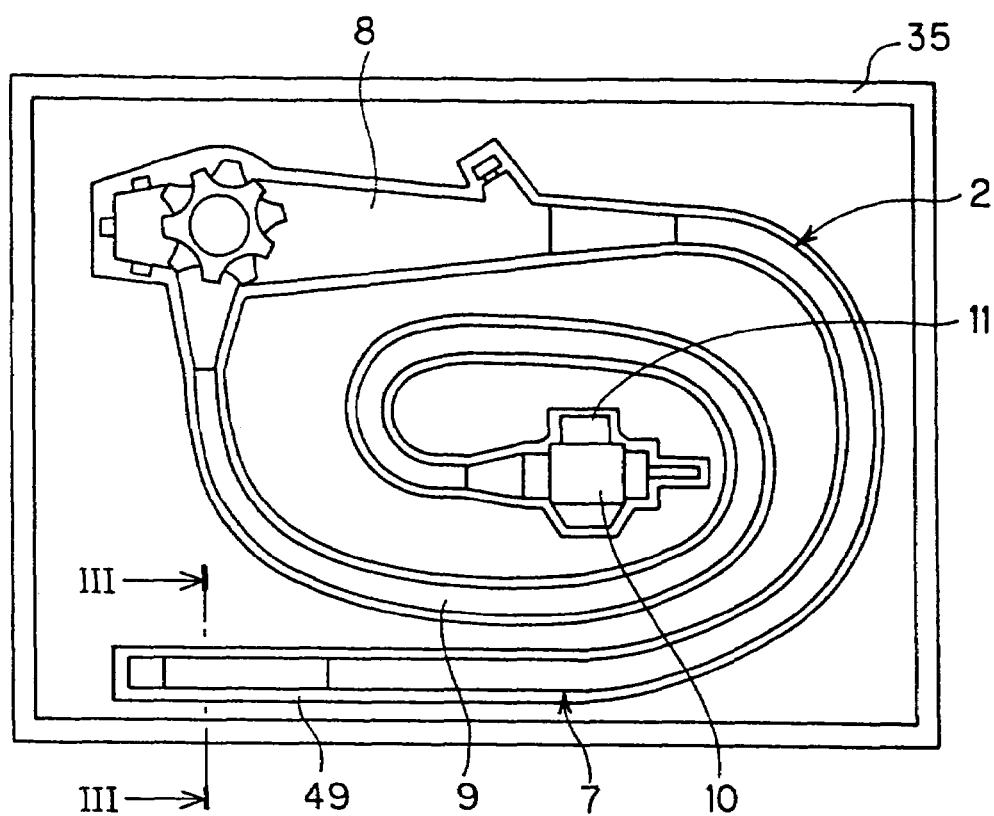
FIG. 15 is a plan view showing the state in which the endoscope according to the third embodiment is stored in a tray.
Figure 16:
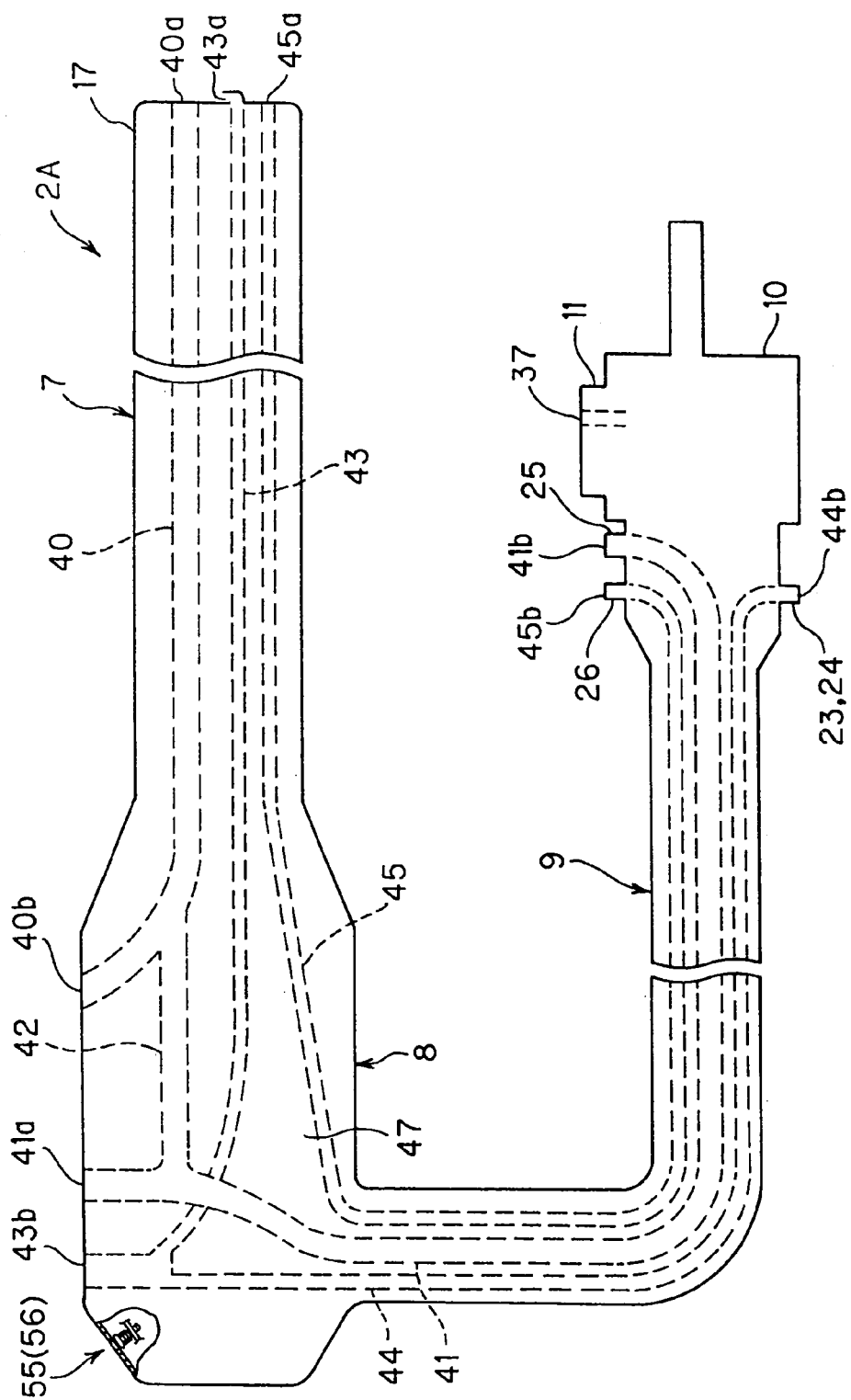
FIG. 16 is a diagram showing the configuration of a channel system disposed in the endoscope according to the third embodiment.
Figure 17:
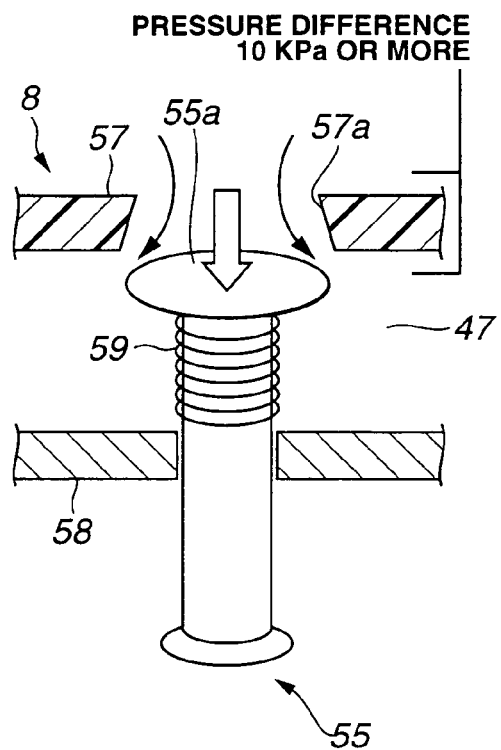
FIG. 17 is a schematic configuration diagram for explaining the structure and the operation of a steam supply check valve disposed in the endoscope according to the third embodiment.
Figure 18:
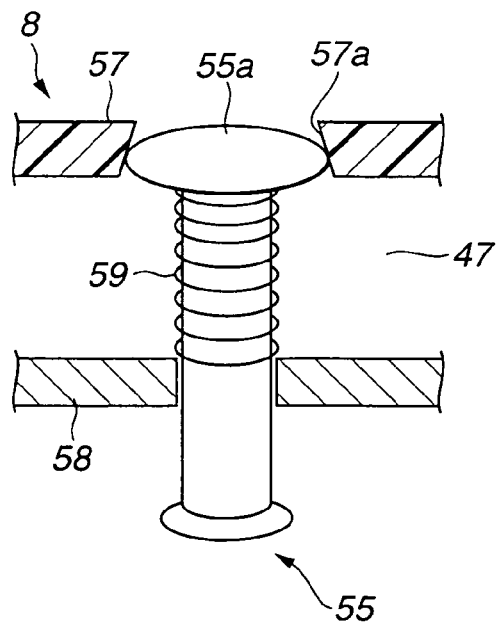
FIG. 18 is a schematic configuration diagram for explaining the structure and the operation of the steam supply check valve disposed in the endoscope according to the third embodiment.
Figure 19:
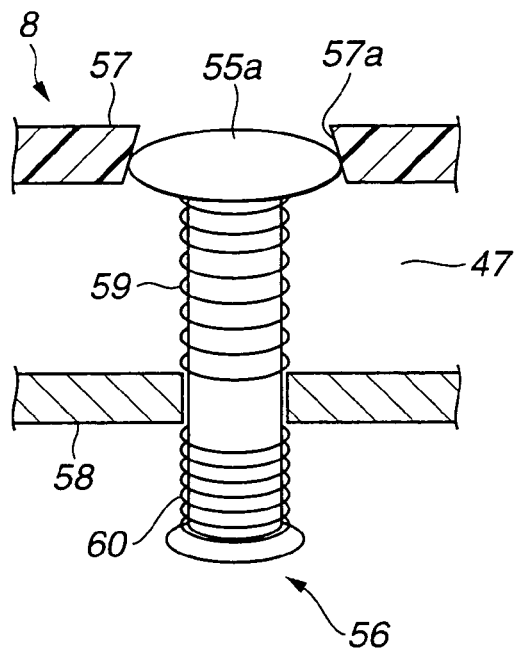
FIG. 19 is a schematic configuration diagram for explaining the structure and the operation of a steam supply temperature valve disposed in the endoscope according to the third embodiment.
Figure 20:
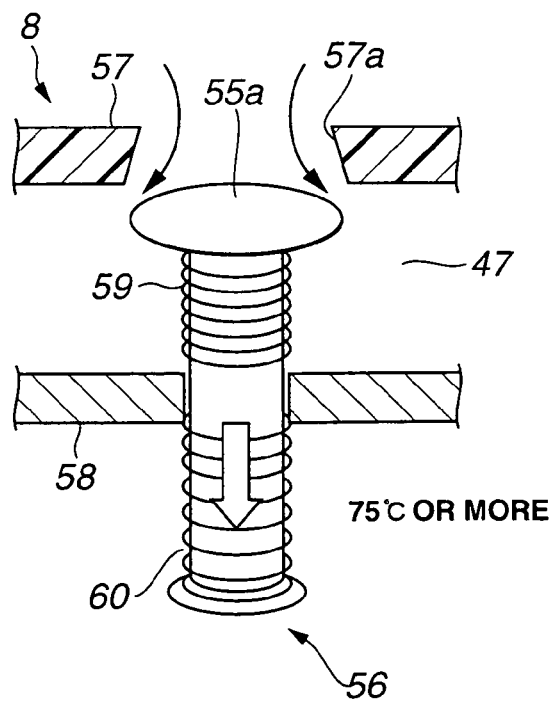
FIG. 20 is a schematic configuration diagram for explaining the structure and the operation of the steam supply temperature valve disposed in the endoscope according to the third embodiment.
Figure 21:
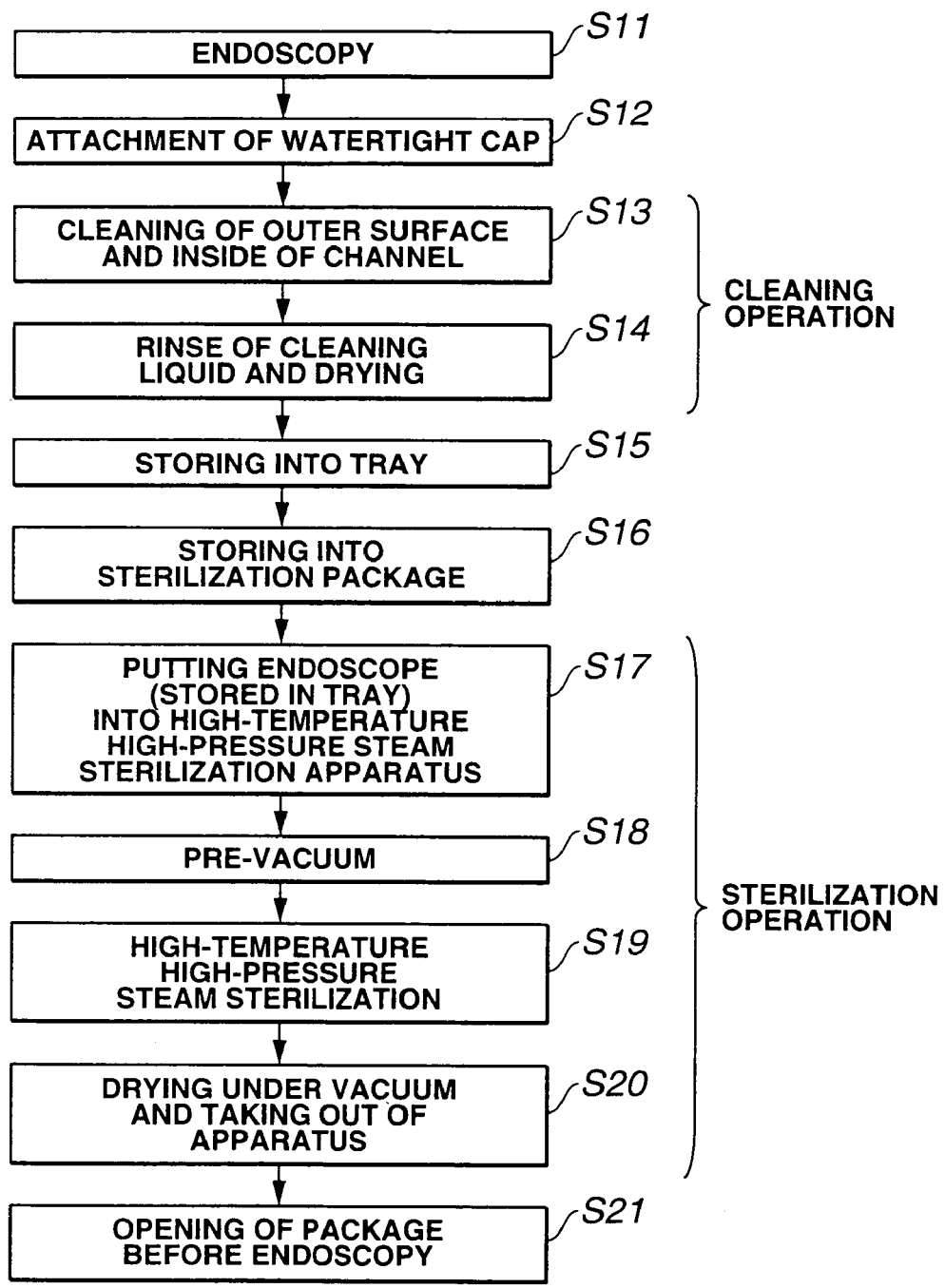
FIG. 21 is a flow chart showing a treatment procedure of reprocessing in which a treatment is performed in order that reuse after endoscopy becomes possible, according to the third embodiment.
Figure 22:
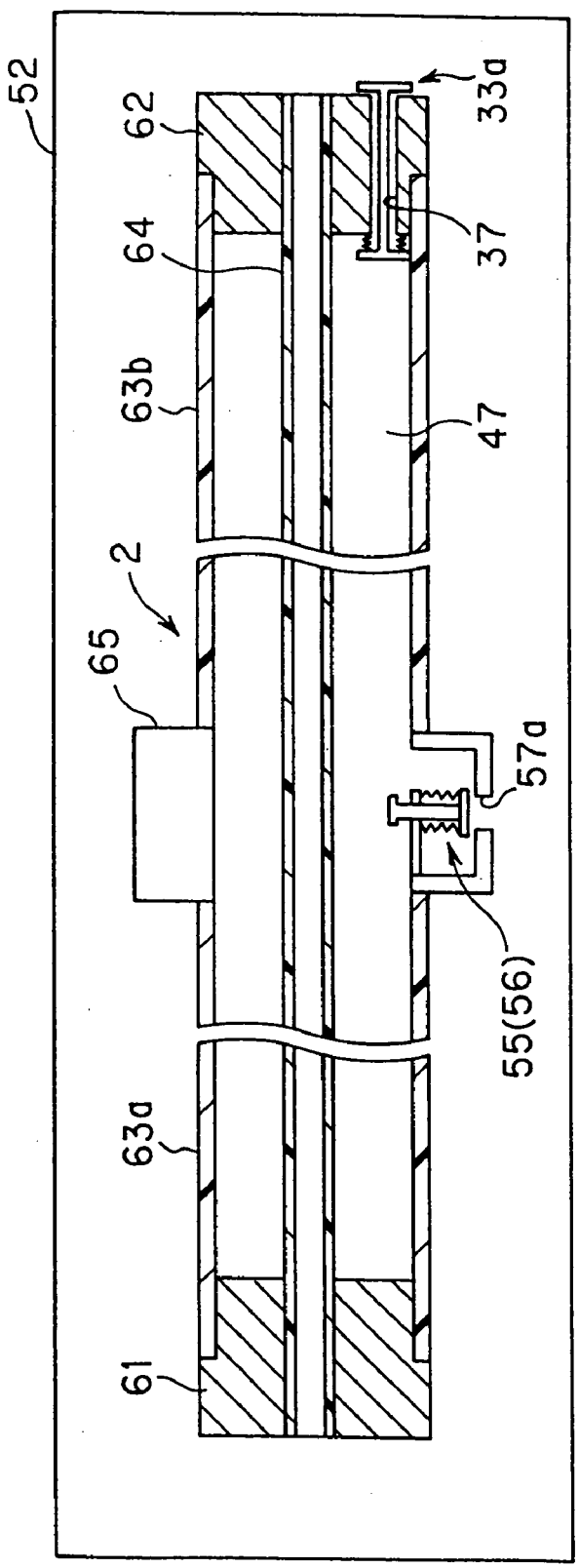
FIG. 22 is a schematic diagram of an endoscope for explaining the operation in the high-temperature high-pressure steam sterilization with the endoscope provided with a steam supply temperature valve.
Figure 23:
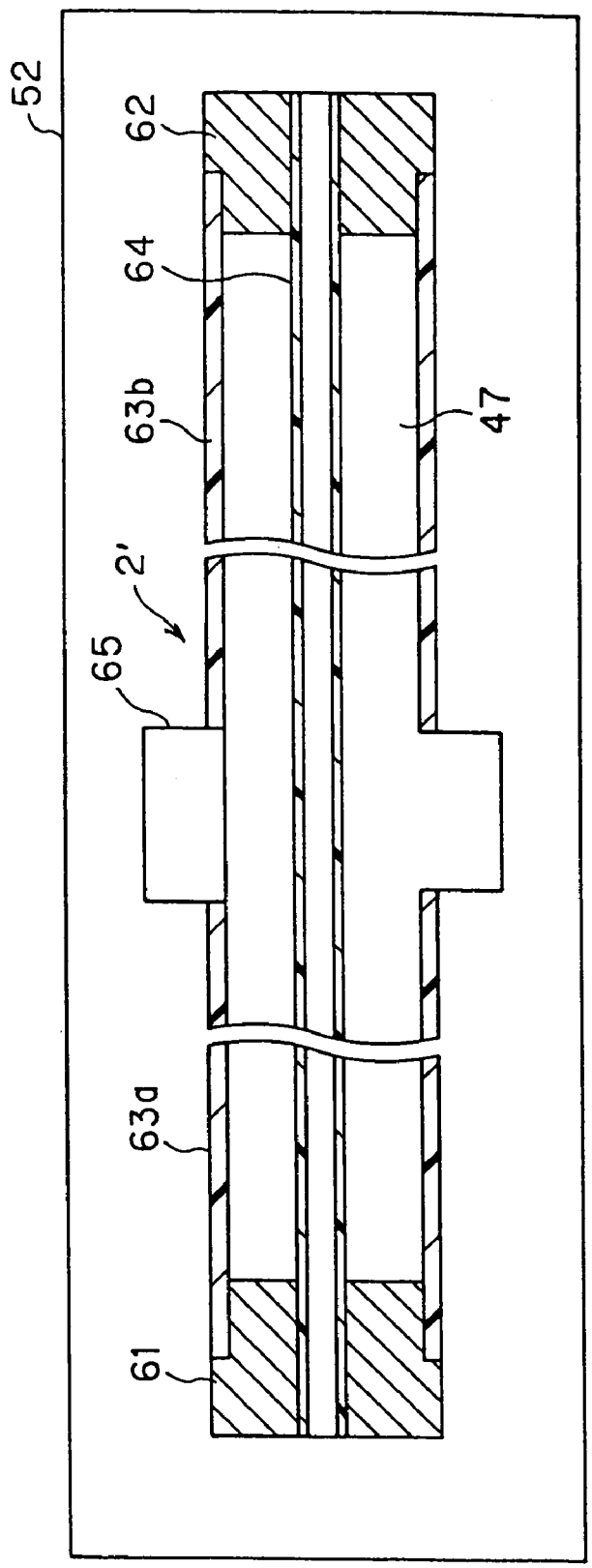
FIG. 23 is a schematic diagram of an endoscope for explaining the operation in the high-temperature high-pressure steam sterilization according to a conventional art.
Figure 24:
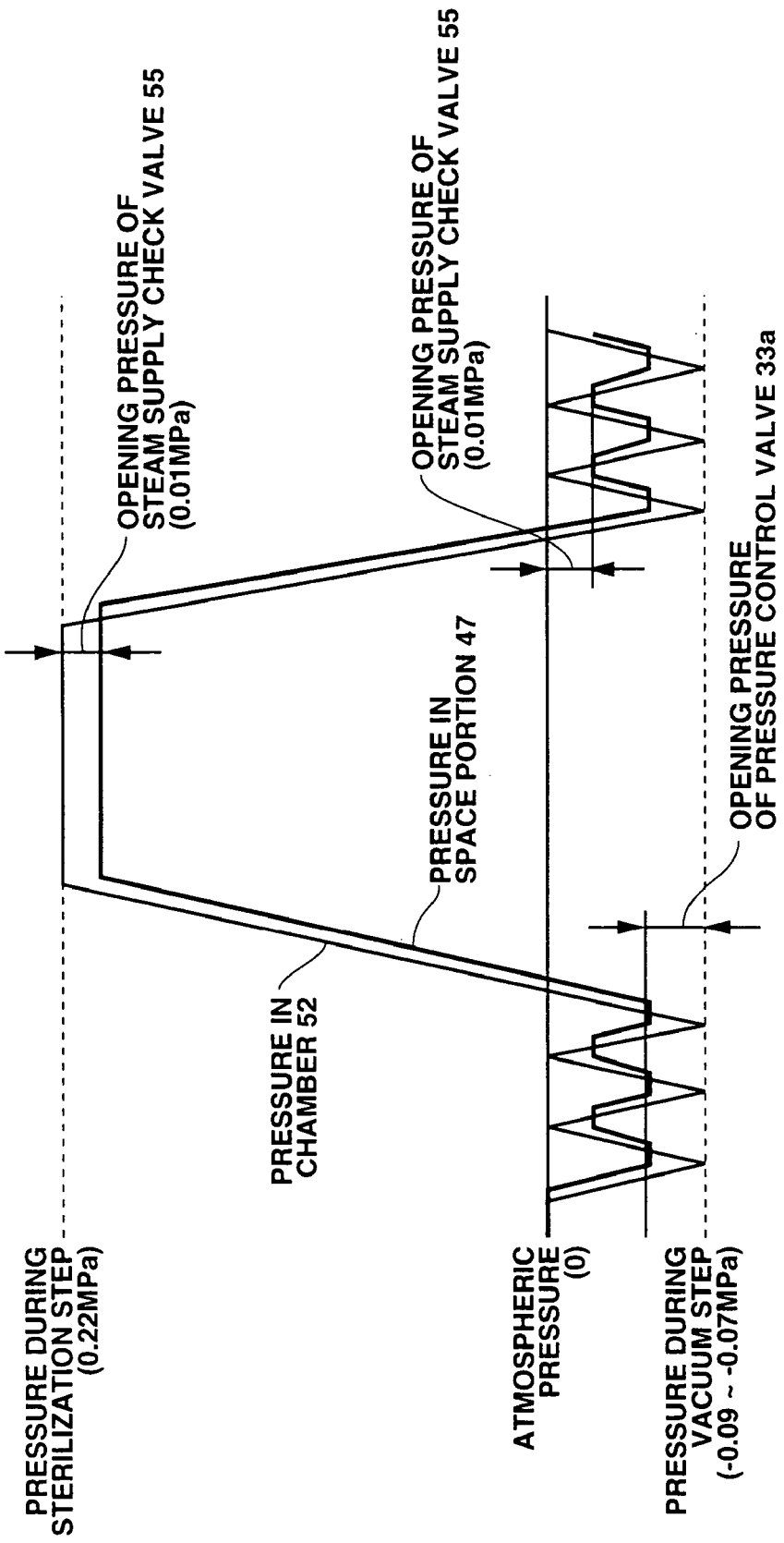
FIG. 24 is a diagram showing the state of pressure in a space portion in the inside of an endoscope during the high-temperature high-pressure steam sterilization.

FIG. 14 to FIG. 24 are diagrams related to a third embodiment of the present invention. FIG. 14 is an entire configuration diagram of an endoscope apparatus provided with an endoscope according to the third embodiment of the present invention. FIG. 15 is a plan view showing the state in which the endoscope according to the third embodiment is stored in a tray. FIG. 16 is a diagram showing the configuration of a channel system disposed in the endoscope according to the third embodiment. FIG. 17 is a schematic configuration diagram for explaining the structure and the operation of a steam supply check valve disposed in the endoscope according to the third embodiment. FIG. 18 is a schematic configuration diagram for explaining the structure and the operation of the steam supply check valve disposed in the endoscope according to the third embodiment. FIG. 19 is a schematic configuration diagram for explaining the structure and the operation of a steam supply temperature valve disposed in the endoscope according to the third embodiment. FIG. 20 is a schematic configuration diagram for explaining the structure and the operation of the steam supply temperature valve disposed in the endoscope according to the third embodiment. FIG. 21 is a flow chart showing a treatment procedure of reprocessing in which a treatment is performed in order that reuse becomes possible after endoscopy, according to the third embodiment. FIG. 22 is a schematic diagram of an endoscope for explaining the operation in the high-temperature high-pressure steam sterilization of the endoscope provided with a steam supply temperature valve. FIG. 23 is a schematic diagram of an endoscope for explaining the operation in the high-temperature high-pressure steam sterilization according to a conventional art. FIG. 24 is a diagram showing the state of pressure in a space portion in the inside of an endoscope during the high-temperature high-pressure steam sterilization.

The same constituents as that in the first embodiment are indicated by the same reference numerals as in the first embodiment, explanations thereof will not be provided, and different points will be primarily described.

The configuration of an endoscope according to the present embodiment will be described. FIG. 14 shows an entire configuration of an endoscope apparatus 1. In FIG. 14, the watertight cap 33 is provided with a pressure control valve 33a in contrast to that in FIG. 1.

In the control section 8 in the endoscope 2 of the third embodiment, a steam supply check valve 55 or a steam supply temperature drive valve 56 (may be abbreviated as a steam supply temperature valve) is disposed in order to flow high-temperature high-pressure steam into the space portion in the inside of the outer covering component of the endoscope 2, under the condition in which high-temperature high-pressure steam sterilization is performed, to heat-sterilizing the space portion in the inside of the endoscope 2 with steam, as described later. With respect to the steam supply check valve 55 (or the steam supply temperature valve 56), a valve is automatically opened at the condition of a high-temperature high-pressure steam (the condition in which the endoscope 2 is present in an atmosphere of high-temperature high-pressure steam).

The high-temperature high-pressure steam sterilization of the endoscope 2 is performed in the state in which the watertight cap 33 with a pressure control valve is attached to the electrical connector portion 11.

In this state, the pressure control valve 33a of the watertight cap 33 with a pressure control valve is closed, the vent hole is blocked by the watertight cap 33 with a pressure control valve, and the inside of the endoscope 2 is watertightly enclosed and is cut off from the outside.

A pre-vacuum step may be performed prior to the step of sterilization treatment with high-temperature high-pressure steam. In this pre-vacuum step, when the pressure in the sterilization chamber is reduced, the pressure in the outside becomes lower than the pressure in the inside of the endoscope 2 and, therefore, pressure difference occurs. When this pressure difference occurs, the pressure control valve is opened and, therefore, the inside of the endoscope 2 communicates with the outside through the vent hole 37. Consequently, occurrence of a large pressure difference between the inside of the endoscope 2 and the sterilization chamber (that is, chamber 52) is prevented. In this manner, breakage of the endoscope 2 due to the pressure difference between the inside and the outside does not occur.

In the sterilization step, when the inside of the sterilization chamber is pressurized and, therefore, such a pressure difference that the pressure in the outside becomes higher than the pressure in the inside of the endoscope 2 occurs, the pressure control valve is closed. In this manner, the high-temperature high-pressure steam does not actively enter the inside of the endoscope 2 through the watertight cap 33 with a pressure control valve and the vent hole.

Various channels built in the inside of the endoscope 2 according to the present embodiment are substantially similar to the channels shown in FIG. 5, but are different in the following point.

With respect to the feature of the present embodiment, the steam supply check valve 55 or the steam supply temperature (drive) valve 56 is disposed in, for example, the control section 8 located in the neighborhood of the midpoint of the channel extending from the connector portion 10 to the distal end portion 17 of the insertion portion 7. In the high-temperature high-pressure steam sterilization, this valve allows high-temperature high-pressure steam to flow into the inside space portion 47 enclosed by the outer covering component, e.g., the integument, of the endoscope 2 so as to perform (heat) sterilization, and when the condition fits into that of a high-temperature high-pressure steam sterilization, the valve is opened, so that the space portion 47 is made to communicate with the outside.

In FIG. 16, the steam supply check valve 55 (or the steam supply temperature valve 56) is disposed in the vicinity of the back end of the control section 8.

In the electrical connector portion 11, the space portion 47 communicates with the outside through the vent hole 37. Therefore, the watertight cap 33 with a pressure control valve is attached to the electrical connector portion 11 during the cleaning and the sterilization. In the state in which the watertight cap 33 is attached to the electrical connector portion 11, the space portion 47 communicates with the outside through the pressure control valve 33a.

FIG. 17 to FIG. 20 show the schematic configurations of the steam supply check valve 55 and the steam supply temperature valve 56.

As shown in FIG. 17, the outer surface of the control section 8 is provided with an opening 57a disposed in the control section outer covering component 57. The steam supply check valve 55 serving as a pressure drive valve, which is opened in a pressurization step of the high-temperature high-pressure steam sterilization so as to communicate with the outside, is disposed in the space portion 47 in the inside of the endoscope 2 inside the opening 57a. With respect to the location of disposition of the steam supply check valve 55, the effect is exerted as long as the check valve 55 communicates with the space in the periphery of the middle portion of the channel in the inside of the endoscope 2. However, it is more effective that the check valve 55 is disposed in the control section 8 located in the neighborhood of the midpoint between the distal end portion 17 of the insertion portion 7 and the connector portion 10.

The end portion of the steam supply check valve 55 is inserted through a hole disposed in a valve support frame 58 fixed to the inside of the control section 8, while being free to move forward and backward, and the valve portion 55a disposed at the upper end is energized by the elastic force of a watertightness-ensuring spring 59 to press-contact the opening 57a. In the normal state, specifically, at a water pressure during the endoscopy and the cleaning step, as shown in FIG. 18, the steam supply check valve 55 is not opened and, thereby, the space portion 47 is cut off from the outside, so that the watertightness is ensured by the steam supply check valve 55.

In the pressurization step of the high-temperature high-pressure steam sterilization, when the pressure in the chamber 52 is higher than the pressure in the space portion 47 in the inside of the control section 8 by 0.01 MPa or more, the valve portion 55a is pressed and opened as shown in FIG. 17. It is essential only that the pressure difference which causes the opening is designed to be higher than the water pressure (here, 0.001 MPa) during the cleaning step and lower than the maximum pressure (here, 0.2 MPa) in the chamber 52 during the sterilization step. However, 0.005 MPa or more and 0.05 MPa or less is more preferable in order to more reliably ensure the watertightness up to the cleaning step and to open for longer time during the sterilization step.

FIG. 19 and FIG. 20 show the steam supply temperature valve 56. This valve exerts the effect similar to that of the steam supply check valve 55 in the high-temperature high-pressure steam sterilization, and serves as a temperature drive valve in which the valve is opened at the temperature in the high-temperature high-pressure steam sterilization.

The steam supply temperature drive valve 56 has a structure in which an SMA (shape-memory alloy) spring 60 is further disposed in the structure of the steam supply check valve 55.

That is, with respect to the steam supply check valve 55, the watertightness-ensuring spring 59 is disposed between the valve support frame 58 and the control section outer covering component 57 and, thereby, the steam supply check valve 55 is energized to the opening 57a side. On the other hand, the steam supply temperature drive valve 56 is further energized by the SMA spring 60 disposed in the side lower (the side inner) than the valve support frame 58 in the direction opposite to the energization direction by the watertightness-ensuring spring 59.

In the normal state, that is, at a water pressure during the endoscopy and the cleaning step, the steam supply temperature drive valve 56 is not opened due to the elastic force of the watertightness-ensuring spring 59 and, therefore, the state shown in FIG. 19 is maintained.

On the other hand, in the high-temperature high-pressure steam sterilization step, the SMA spring 60 exerts a restoring force (elastic force) larger than the elastic force of the watertightness-ensuring spring 59.

For example, when the temperature rises to 75° C. or more, the SMA spring 60 exerts a restoring force larger than the elastic force of the watertightness-ensuring spring 59, and, as shown in FIG. 20, the steam supply temperature drive valve 56 is opened. With respect to the temperature condition at which the restoring force to open the valve is exerted, it is essential only that the temperature is higher than the water temperature (for example, 65° C.) during the cleaning step and lower than the maximum temperature (for example, 135° C.) in the chamber 52 during the sterilization step. However, 70° C. or more and 100° C. or less is more preferable in order to more reliably ensure the watertightness up to the cleaning step and to open for longer time during the sterilization step. In FIG. 20, the temperature is shown as 75° C. For example, a Ni—Ti alloy can be used as the SMA.

A filter which passes steam but does not pass objects larger than or equal to some extent of size may be disposed, although not shown in the drawing, in the steam path of the steam supply check valve 55 or the steam supply temperature valve 56.

A series of steps performed in the high-temperature high-pressure steam sterilization apparatus 50 is similar to that in the above-described FIG. 7 and, therefore, explanations thereof will not be provided.

As is described below with reference to FIG. 21, after the endoscopy is completed, the cleaning of the endoscope 2 is performed. At this time, the watertight cap 33 with a pressure control valve is attached to the electrical connector portion 11 of the endoscope 2 and, thereby, the cleaning liquid is prevented from entering the inside of the endoscope 2 and being brought into contact with the contact pins 38 of the electric signal that may cause deterioration of the surfaces of the contact pins 38 (failure in current-carrying and the like) in the future. After the cleaning step is completed, the endoscope 2 is stored in the tray 35 while taking a predetermined shape, and the sterilization step is performed.

Furthermore, a filter which passes steam but does not pass objects larger than or equal to some extent of size may be disposed, although not shown in the drawing, in the communication path of the pressure control valve 33a of the watertight cap 33 with a pressure control valve.

The operations of the present embodiment will be described below with reference to FIG. 21. FIG. 21 shows each step performed in the reprocessing of the endoscope 2 in detail.

As shown in step S11, the endoscopy is performed with the endoscope 2. After this endoscopy is completed, as shown in step S12, the watertight cap 33 with pressure control valve 33a is attached to the electrical connector portion 11, so that the watertightness of the endoscope 2 is ensured. Subsequently, a cleaning operation (cleaning step) composed of step S13 and step S14 is performed.

In step S13, the outer surface of the endoscope 2 and inside of the channels are cleaned. Thereafter, as shown in step S14, a rinse of a cleaning liquid and drying are performed.

After this cleaning operation of step 13 and step 14 is completed, as shown in step S15, the endoscope 2 is stored in the tray 35 while the watertight cap 33 with a pressure control valve is left attached.

Subsequently, as shown in S16, the tray 35 including the endoscope 2 is stored in a sterilization package, e.g., a peel package.

The endoscope 2 stored in the sterilization package is put into the high-temperature high-pressure steam sterilization apparatus 50 shown in FIG. 6 (step 17), and the sterilization operation (sterilization step) from step S17 to step S20 is performed.

At this time, the user is not required to perform any special operation with respect to the endoscope 2, and only performs relocation. Therefore, a shift to the sterilization can be performed more promptly, and the following sterilization does not become inadequate due to misoperation.

A pre-vacuum (vacuum) treatment of step S18 is performed prior to performing a high-temperature high-pressure steam sterilization of step S19 with the high-temperature high-pressure steam sterilization apparatus 50.

During this pre-vacuum step, the inside of the chamber 52 is brought into a vacuum state, and then the pressure is returned to an original pressure while high-temperature high-pressure steam is supplied.

At this time, since the pressure control valve 33a is disposed, the inside of the endoscope 2 becomes into a vacuum state together with the inside of the chamber.

This process is performed at least once and, thereafter, the chamber 52 and the space portion 47 in the endoscope 2 are pressurized, so that a steam sterilization step is performed.

Desirably, the pre-vacuum step is performed plural times because air is adequately discharged from the chamber 52 and the space portion 47 in the endoscope 2 and, thereby, steam readily substitutes for the air during the high-temperature high-pressure steam sterilization step in the following step S19.

After the high-temperature high-pressure steam sterilization, it is desirable that the drying step under vacuum of step S20 is performed.

By this drying step, steam entered in the space portion 47 of the endoscope 2 can be removed through the pressure control valve 33a, no moisture remains in the endoscope 2, and the durability of constituents in the endoscope 2 can be maintained. Consequently, the deterioration due to rust and moisture can be minimized. Then, the endoscope 2 is taken out of the high-temperature high-pressure steam sterilization apparatus 50.

Before the endoscope 2 taken out of the high-temperature high-pressure steam sterilization apparatus 50 is used for endoscopy, as shown in step S21, the sterilization package is opened and the endoscope 2 is taken out. Subsequently, the endoscope 2 can be used for the endoscopy.

The operations by the steam supply check valve 55 or the steam supply temperature valve 56 will be described below with reference to FIG. 22 and FIG. 23.

FIG. 22 schematically shows the configuration of the endoscope 2 in the chamber 52, and for purposes of comparison, FIG. 23 shows the configuration of the endoscope 2' in the chamber 52 according to a conventional art. FIG. 22 shows the state in which the space portion 47 in the inside of the endoscope 2 communicates with the inside of the chamber 52 by the steam supply check valve 55. In the case of the steam supply temperature drive valve 56, the steam supply check valve 55 can simply be read as the steam supply temperature drive valve 56.

The endoscope 2' shown in FIG. 23 is composed of end portions 61 and 62, integument tubes 63a and 63b fixed thereto, a channel 64 (for example, a simulation of the channel 45), both ends of which are opened at the end portions 61 and 62 and which is stored in the integument tubes 63a and 63b, the space portion 47, and a joint portion 65 (a simulation of the control section 8) connecting the two integument tubes 63a and 63b in the neighborhood of the middle portion of the channel 64.

In the endoscope 2 shown in FIG. 22, the pressure control valve 33a is disposed in the end portion 62, and the steam supply check valve 55 is disposed in the joint portion 65 in the configuration shown in FIG. 23. Put another way, in the endoscope 2' according to the conventional art shown in FIG. 23, the steam supply check valve 55 or the steam supply temperature drive valve 56 is not disposed, and in the high-temperature high-pressure steam sterilization step, the endoscope 2' becomes in the state of being enclosed watertightly.

In the state shown in FIG. 23, since the space portion 47 is an enclosed space different from the chamber 52, even in the high-temperature high-pressure sterilization step, the pressure in the space portion 47 is not increased relative to the inside of the chamber 52, and the temperature is resistant to rising as well.

Consequently, even when steam enters into the channel 64 after the pre-vacuum, the temperature of the steam becomes resistant to rising as the steam goes into the deep of the space portion 47, that is, as the steam goes to the location farther from the end portion 61 and the end portion 62, for example, the neighborhood of the inside of the joint portion 65. This is because the temperature is readily lowered by the space portion 47 midway through the channel 64. Therefore, it may take a significantly long time to reliably perform sterilization.

Generally in many cases, endoscopy is performed plural times in the same day and, in many cases, the endoscope used in the first inspection is reprocessed and used on several occasions in the same day. At that time, it is desired that the reprocessing can be performed promptly and reliably as much as possible.

The operations of the endoscope 2 shown in FIG. 22, according to the present embodiment, will be described. Since the pressure control valve 33a and the steam supply check valve 55 are disposed, the pressure in the space portion 47 exhibits the behavior shown in FIG. 24.

By the pre-vacuum step, air in the space portion 47 is discharged from the pressure control valve 33a, and a vacuum is produced, so that steam readily enters from the steam supply check valve 55 during the sterilization step after the pre-vacuum step.

Subsequently, steam enters from the steam supply check valve 55 into the space portion 47 in the temperature raising and heating (steam supply) step. Since the steam supply check valve 55 is disposed in the joint portion 65 close to the middle portion of the channel 64, the steam entered from the steam supply check valve readily goes throughout the space portion 47.

Therefore, with respect to the inside of the chamber 52 and the space portion 47, the pressures readily become substantially equal, and substantially equivalent steam presents. Consequently, even a deep position of the channel 64 is applied with heat from the outside of the joint portion 65 at a level similar to that in the chamber 52 as well, so that every position in the joint portion 65 can be sterilized promptly. An important factor of the vent path of the pressure control valve 33a, the steam supply check valve 55, and the steam supply temperature drive valve 56 is the sizes of the steam paths thereof.

The steam path of the vent path of the pressure control valve 33a is assumed to be very small (for example, a path of 0.1 mm in diameter) relative to the volume of the space portion 47. As a result, the space portion 47 cannot synchronize to the speed of the pressure change in the chamber 52, and a time lag occurs.

In the pre-vacuum step, for example, even when the state of −0.08 MPa is repeated 3 times in the chamber 52, the step of pressure increase may start in the chamber 52 in spite of the fact that the inside of the space portion 47 is lowered only to −0.03 MPA, for example.

Consequently, since the inside of the space portion 47 is insufficiently subjected to prevacuum, the air originally present in the space portion 47 remains significantly, and therefore the substitution of steam may be insufficient.

In this case, if the inside of the chamber 52 is kept at a minimum pressure for longer time, the pressure in the space portion 47 becomes a similar pressure in the end. However, the increase in time is a direction opposite to the state required by the user.

Likewise, in the temperature raising and heating step and the sterilization step, if the steam path of the steam supply check valve 55 or the steam supply temperature drive valve 56 is very small, even when the inside of the chamber 52 reaches 0.22 MPA, the inside of the space portion 47 takes a long time to reach and, therefore, delays. As a result, the sterilization time (maximum temperature state) must be long-extended in order to achieve sterilization. This is a direction opposite to the state required by the user as well.

In this manner, the steam paths of the pressure control valve 33a, the steam supply check valve 55, and the steam supply temperature drive valve 56 tends to have adequately large size relative to the volume of the space portion 47.

The larger size, for example, of 1 mm or more in diameter, if possible, of 5 mm or more in diameter, or of 10 mm or more in diameter, is more desirable.

If possible, the path areas of the pressure control valve 33a, the steam supply check valve 55, and the steam supply temperature drive valve 56 are larger than the clearance area of the portion having a minimum clearance among the space portion 47 in the inside of the endoscope 2, communicating with the pressure control valve 33a and the steam supply check valve 55 or the steam supply temperature drive valve 56, because the pressure control valve 33a, the steam supply check valve 55, and the steam supply temperature drive valve 56 can be prevented from becoming a bottleneck in the path.

As described above, in the present embodiment, the steps are made to progress while the pressures in the chamber 52 and the space portion 47 in the endoscope 2 are always substantially equal during the pre-vacuum step and the high-temperature high-pressure steam sterilization step. Consequently, the sterilization in the channel can be reliably performed in a minimum time.

When a filter which passes steam but does not pass objects having some extent of size is disposed in the steam paths of the pressure control valve 33a, the steam path of the steam supply check valve 55, and the steam supply temperature drive valve 56, a lubricant used in the endoscope 2, dust, and the like can be perfectly prevented from flowing to the outside during sterilization operation.

Therefore, according to the present embodiment, the sterilization in channels built in the endoscope 2 can be performed more promptly and reliably.

Fourth Embodiment

A fourth embodiment of the present invention will be described below with reference to FIG. 25 to FIG. 27. In the third embodiment, the steam supply check valve 55 or the steam supply temperature drive valve 56 is disposed and, thereby, high-temperature high-pressure steam is flowed into the inside of the endoscope 2 during the high-temperature high-pressure steam sterilization, so that the space portion 47 in the inside can be subjected to superheat sterilization. However, in the present fourth embodiment, an apparatus to heat the channel by heat generation is disposed.

Figure 25:
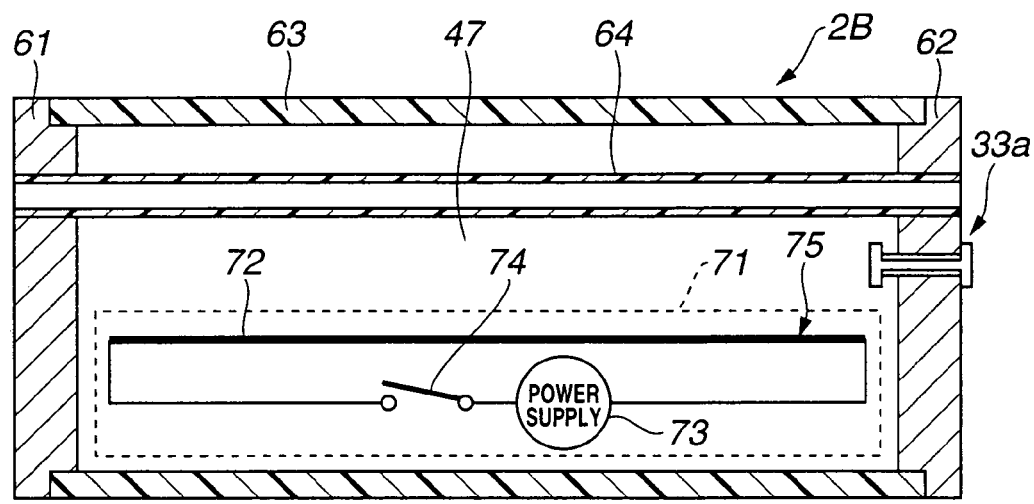
FIG. 25 is a configuration diagram schematically showing the configuration of an endoscope and a heat generator built in this endoscope according to a fourth embodiment.

FIG. 25 schematically shows the configuration of an endoscope 2B and a heat generator 71 built in the endoscope 2B according to the fourth embodiment. In a manner substantially similar to that shown in FIG. 22, in the endoscope 2B, a space portion 47 cut off from the outside is constructed by end portions 61 and 62, an integument tube 63 which is fixed thereto and serves as an outer covering member, and a channel 64, both ends of which are opened at the end portions 61 and 62 and which is stored in the integument tube 63, in the inside of the endoscope 2B. In FIG. 25, the integument tubes 63a and 63b and the joint portion 65 shown in FIG. 22 and FIG. 23 are typified by the integument tube 63. A pressure control valve 33a is attached to the end portion 62.

In the present embodiment, the heat generator 71 is stored in the space portion 47. The heat generator 71 is composed of a heating wire 72, a circuit power supply 73, and an electric circuit 75 including a switch 74.

When the switch 74 is off, the electric circuit 75 is interrupted by the switch 74. The current from the power supply 73 passes through the electric circuit 75 while the switch 74 is on, and the heating wire 72 generates heat.

The switch 74 is off at normal temperatures, and is designed to be switched on when heated.

Figure 26:
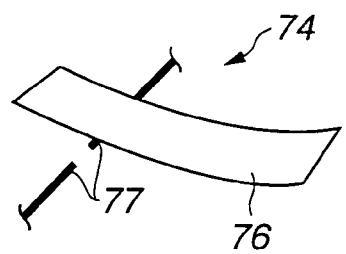
FIG. 26 is an explanatory diagram showing the state in which a switch is opened, for explaining the function of the switch built in the endoscope shown in FIG. 25.
Figure 27:
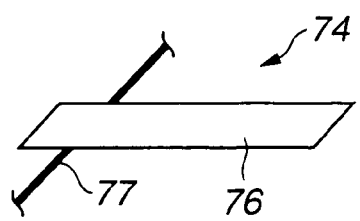
FIG. 27 is an explanatory diagram showing the state in which the switch is closed, for explaining the function of the switch built in the endoscope shown in FIG. 25.

As shown in FIG. 26 and FIG. 27, the switch 74 is made of a shape-memory alloy spring (hereafter referred to as SMA spring 76), the shape of which varies in response to high temperatures, and the SMA spring 76 shown in FIG. 26 is in the state of being disconnected from a contact 77 connected to the heating wire 72 at normal temperatures and, therefore, is off.

When the temperature becomes high, the shape of the SMA spring 76 varies and, thereby, the SMA spring 76 is brought into contact with the contact 77, so that the switch 74 is switched on, as shown in FIG. 27. Here, a NiTi alloy is adopted as an example of the SMA spring 76.

It is preferable that the switch 74 can be turned on at a temperature higher than the water temperature (for example, 65° C.) during the cleaning step and lower than the maximum temperature (for example, 135° C.) in the chamber 52 during the sterilization step. However, it is more preferable that the switch 74 is turned on at a temperature of 70° C. or more and 100° C. or less in order to more reliably ensure the watertightness up to the cleaning step and to open for longer time during the sterilization step. Here, the switch 74 is adjusted to be turned on at 75° C. or more.

The heat generator 71 may be disposed throughout the inside of the endoscope 2B, or be disposed in a part thereof. It is desirable that the heat generator 71 is disposed in the neighborhood of the middle portion of the channel when disposed in a part of the inside.

The operations in the present embodiment will be described below.

In the high-temperature high-pressure steam sterilization step, the sterilization subject is heated by direct contact with steam and, thereby, is sterilized. The outer surface of the endoscope 2B is brought into direct contact with steam and, thereby, is readily heated. However, the space portion 47 surrounded by the channel 64 and the outer surface of the endoscope 2B is an enclosed space and, therefore, steam does not enter, so that the space portion 47 is resistant to being heated. Consequently, the temperature rising rate of the space portion 47 is lower than that of the portion brought into direct contact with steam.

On the other hand, since the end portions 61 and 62 of the channel 64 in the inside of the endoscope 2B are opened to the space outside the endoscope 2B, steam enters the channel 64. However, since the temperature rising rate of the space portion 47 located in the periphery of the channel 64 is low, the heat of the steam entered into the channel 64 is diffused into the space portion 47 and, therefore, the temperature in the channel 64 is resistant to rising. Consequently, the sterilization tends to take time in the channel 64.

Here, a case where the heat generator 71 is built in the inside of the endoscope 2B will be described.

The heat generator 71 is designed to generate heat by the heat applied during the high-temperature high-pressure sterilization step.

As described above, when the temperature becomes 75° C. or more, the switch 74 of the heat generator 71 is turned on, and the heat generator 71 starts the heat generation. The heat delivered from the heat generator 71 heats the space portion 47 and the temperature is raised.

When the temperature of the space portion 47 is raised, the heat of the steam entered into the channel 64 is resistant to diffusing into the space portion 47, or when the temperature of the space portion 47 becomes higher than the temperature in the channel 64, the channel 64 can be heated by the heat in the space portion 47 in addition to the heat of the steam. As a result, the temperature in the channel 64 tends to be raised, and the sterilization tends to be performed promptly.

When the sterilization step is completed, the heating by the steam is terminated, and the space temperature in the periphery of the endoscope 2B is decreased. Accompanying that, the temperature of the space portion 47 is lowered, and the heat generator 71 is also cooled. When the heat generator 71 is cooled and the temperature becomes lower than the switching temperature of the switch 74, the switch 74 is turned off and the heat generator 71 stops the heat generation.

Since a wide range of heating can more effectively advance the sterilization, it is most desirable that the heat generator 71 is disposed throughout the inside of the endoscope 2B. However, if the amount of built-in members in the endoscope 2B is increased, there is a demerit that the endoscope 2B becomes upsized. Therefore, it is desirable that the amount of built-in members in the endoscope 2B is minimized. The following method is also conceived as a method for exerting the effect by disposing the heat generator 71 only in a part of the endoscope.

In the high-temperature high-pressure steam sterilization, the steam is resistant to reach the portion locates farther from the opening of the channel 64, that is, the deeper portion in the channel 64, and therefore, the sterilization takes time. Consequently, it is desirable that the heat generator 71 is disposed at the location apart from the opening of the channel 64, that is, in the neighborhood of the middle portion of the channel.

Therefore, according to the present embodiment, the sterilization of the inside of the channel 64 built in the endoscope 2B can be performed more promptly and reliably.

Fifth Embodiment

Figure 28:
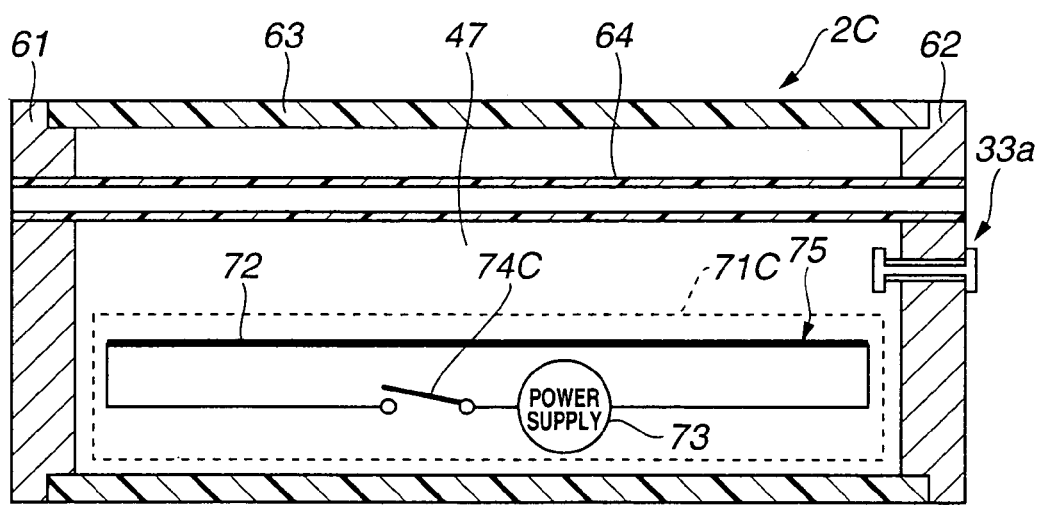
FIG. 28 is a configuration diagram schematically showing the configuration of an endoscope 2C and a heat generator 71C, according to a fifth embodiment.

FIG. 28 schematically shows the configuration of an endoscope 2C and a heat generator 71C according to a fifth embodiment. The heat generator 71C has a configuration in which a switch 74C is adopted in place of the switch 74 in the heat generator 71 shown in FIG. 25.

The structure of the heat generator 71C is equivalent to the structure shown in FIG. 25 except for the switch 74C.

The switch 74C is off at normal pressures, and is designed to be switched on when the endoscope 2C is applied with a pressure higher than normal pressures.

The switch 74C is disposed on the outer surface 78 covered with a hard member, for example, the control section 8 or the connector portion 10 of the endoscope 2C, among the constituents of the endoscope 2C.

Figure 29:
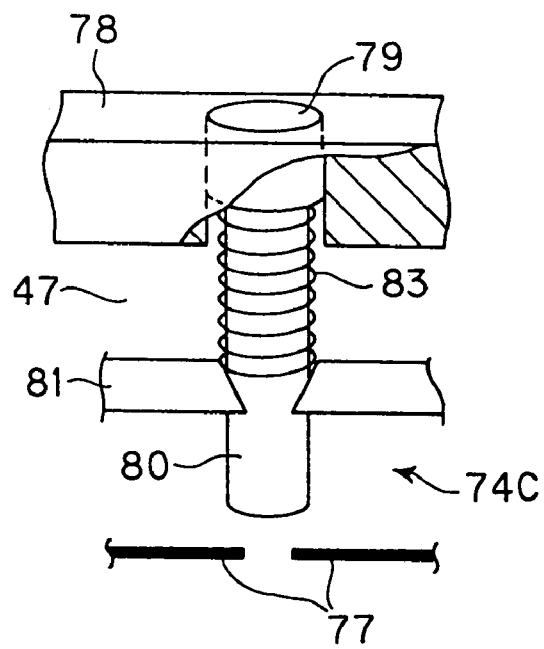
FIG. 29 is a configuration diagram showing the state in which a switch built in the endoscope shown in FIG. 28 is opened.
Figure 30:
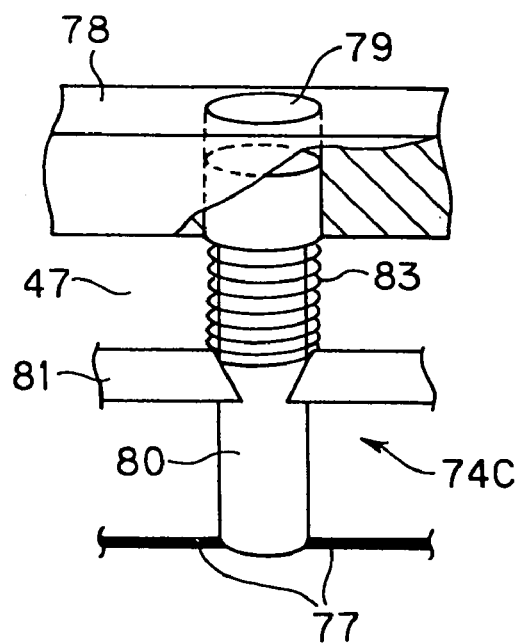
FIG. 30 is a configuration diagram showing the state in which the switch built in the endoscope shown in FIG. 28 is closed.

FIG. 29 and FIG. 30 show the configuration of the switch 74C.

The switch 74C is composed of a switch head 79 in which the top portion is exposed to an opening of the outer surface 78 of the endoscope 2C, a switch rod 80 which is a conductor fixed to the switch head 79, a switch holder 81 supporting the switch rod 80, and a spring 83 located between the switch head 79 and the switch holder 81.

The switch head 79 maintain the watertightness at the interface to the outer surface 78 of the control section 8 or connector portion 10 located in the periphery of the switch head 79, and slides while maintaining the watertightness.

The switch head 79 tends to be pressed in by the pressure applied to the top portion thereof. When the elastic force of the spring 83 is larger than the force pressing the switch head 79, the switch rod 80 is disconnected from the contact 77 constituting the circuit and, therefore, the switch 74C is in the state of off, as shown in FIG. 29.

However, when a high pressure is applied to the head top portion of the switch head 79 during the high-temperature high-pressure steam sterilization step and the force pressing the switch head 79 becomes larger than the elastic force of the spring 83, the switch rod 80 is pressed in together with the switch head 79, the switch rod 80 is brought into contact with the contact 77 constituting the circuit and, therefore, the switch 74C is turned on, as shown in FIG. 30.

The pressure at which the switch 74C of the heat generator 71C is turned on can be controlled by the use of the springs 83 having different elastic forces or by adjusting the spacing between the outer surface 78 and the switch holder 81.

In order that the switch 74C is not turned on in any step other than the high-temperature high-pressure steam sterilization step, preferably, the pressure at which the switch 74C is turned on is adjusted at a pressure which is not applied in any step other than the high-temperature high-pressure steam sterilization step, for example, 0.3 kgf/cm$^2$.

The switch 74C must be turned on at a pressure less than or equal to the set pressure of the high-temperature high-pressure steam sterilization.

The switch head 79 and switch holder 81 must be an insulating material in order that no circuit current escapes when the circuit is energized.

Desirably, a cover serving for preventing the switch head 79 from contacting other objects is attached to the exposed portion of the switch head 79 in order to avoid that the switch head 79 is pressed in by the contact with other objects and, thereby, the switch 74C is tuned on in any step other than the high-temperature high-pressure steam sterilization step.

The operations of the present embodiment will be described below.

The heat generator 71C is designed to generate heat by the pressure applied during the high-temperature high-pressure sterilization step.

A specific example will be shown. When the endoscope 2C is brought into the state at a high pressure in the high-temperature high-pressure steam sterilization step, the switch 74C of the heat generator 71C is turned on by the pressure applied to the top portion of the switch head 79, and the heat generator 71C starts the heat generation. The space portion 47 is heated by the heat generation of the heat generator 71C, and the temperature is raised. As a result, the temperature in the channel 64 tends to be raised, and the sterilization tends to be performed promptly.

When the sterilization step is completed and the space pressure in the periphery of the endoscope is decreased, the switch 74C is turned off and the heat generator 71C stops the heat generation.

In the case where the switch 74C is turned on due to temperature, as in the fourth embodiment, residual heat remains in the inside of the endoscope 2C after the high-temperature high-pressure steam sterilization step is completed and, thereby, the heat generator 71 keeps on generating heat for a while.

It is not preferable that the endoscope 2C is unnecessarily heated from the viewpoint of the resistance of the endoscope 2C. On the other hand, since the pressure is decreased promptly after the high-temperature high-pressure steam sterilization step is completed, the heat generator 71C stops the heat generation promptly. Therefore, it is more preferable that the switch 74C is turned on due to pressure from the viewpoint of the resistance of the endoscope 2C.

According to the fifth embodiment, in addition to the effects of the fourth embodiment, the sterilization can be performed while the endoscope 2C is subjected to unnecessary heating to a lesser extent.

Sixth Embodiment

Figure 31:
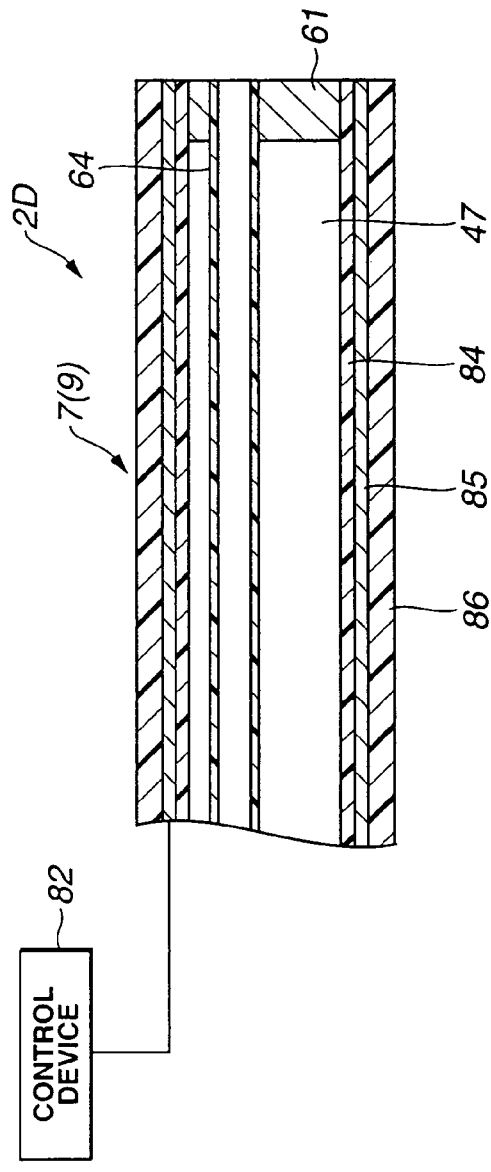
FIG. 31 is a configuration diagram of a heat generator disposed in an insertion portion and the like of an endoscope according to a sixth embodiment of the present invention.

A sixth embodiment of the present invention will be described below. FIG. 31 schematically shows an example of configuration of a slender insertion portion 7 having flexibility, or a connection cord portion 9 having flexibility and a heat generator 71D, of the endoscope 2D.

The heat generator 71D is built in the endoscope 2D, a control device 82 to control the heat generator 71D is disposed in the outside and, thereby, the heat generator 71D is controlled to generate heat during the high-temperature high-pressure steam sterilization step.

The insertion portion 7 and the control section 8 have a multilayer structure composed of a flex 84, a braid 85, and a resin 86. Among them, the braid 85 is used as the heat generator 71D.

A metal having electrical conductivity is used as the material for the braid 85, and the braid is made to generate heat through the use of the property of generating heat by passing current. Specific example of materials for the braid 85 include nichrome alloys and stainless steels.

A part of the braid 85 can be electrically connected to the outside of the endoscope 2D, and is connected to the control device 82 disposed in the outside. The control device 82 is designed to pass the current through the braid 85 during the high-temperature high-pressure steam sterilization step. The control device 82 may be incorporated in the high-temperature high-pressure steam sterilization apparatus 50.

If the current passing through the braid 85 passes through built-in members of the endoscope 2D, the performance of the endoscope 2D might be adversely affected. Therefore, an insulating layer may be disposed between the braid 85 and the built-in members of the endoscope. The flex 84 may be an insulating material, as an example thereof.

The current passing through the braid 85 must be prevented from passing to the outside of the endoscope 2D. Therefore, the resin 86 must have an adequate thickness and the insulation resistance must be increased in order that the current passing through the braid 85 is prevented from leaking.

The operations of the present embodiment will be described below.

The braid 85 is connected to the control device 82 prior to the high-temperature high-pressure steam sterilization step.

The control device 82 passes the current through the braid 85 during the high-temperature high-pressure steam sterilization step, so as to generate heat. When the braid 85 generates heat, the space portion 47 is superheated, and the temperature is raised. As a result, the temperature in the channel 64 tends to be raised, and the sterilization tends to be performed promptly.

When the high-temperature high-pressure steam sterilization step is completed, the control device 82 stops transmission of electrical energy, and the braid 85 stops generation of heat.

In the present embodiment, with respect to the configuration of the heat generator 71D, the circuit power supply 73 and the switch 74 are disposed in the outside. Consequently, built-in members of the endoscope can be reduced, and the endoscope 2D is readily miniaturized compared with that in the fourth and fifth embodiments.

In particular, in the present embodiment, since the built-in member of the conventional endoscope is used as the heat generator 71D, there are advantages that the amount of built-in members of the endoscope 2D is not increased, and the endoscope 2D is not necessarily upsized.

Therefore, according to the present embodiment, in addition to the effects of the fourth embodiment, the heat generator can be disposed without further upsizing the endoscope.

Seventh Embodiment

Figure 32:
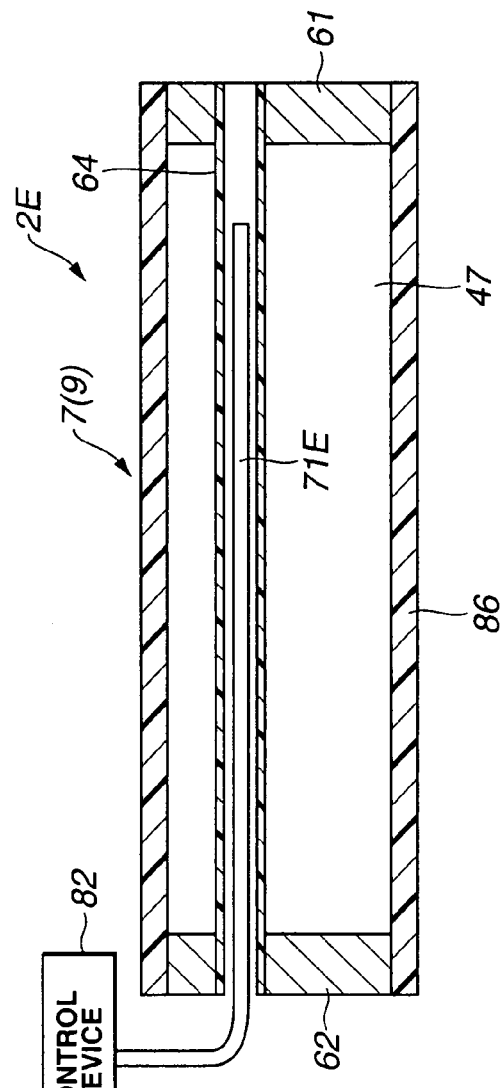
FIG. 32 is a configuration diagram of a heat generator disposed in an insertion portion and the like of an endoscope according to a seventh embodiment of the present invention.

A seventh embodiment of the present invention will be described below with reference to FIG. 32. FIG. 32 schematically shows an endoscope 2E and a heat generator 71E. In the present embodiment, the heat generator 71E is detachably attached to the endoscope 2E.

In this case, the heat generator 71E has a slender shape capable of being inserted into the channel 64 of the endoscope 2E, one end is inserted into the channel 64 of the endoscope 2E, and the other end is connected to the control device 82. The operations of the present embodiment will be described below.

The heat generator 71E is inserted into the channel 64 prior to the high-temperature high-pressure steam sterilization step.

In this case, it is most preferable that the heat generator 71E is inserted into all channels 64 in the endoscope 2E. However, a part of the channels 64 may include the heat generator 71E.

The heat generator 71E is controlled by the control device 82 in order to generate heat during the high-temperature high-pressure steam sterilization step, so that the inside of the channel 64 is directly superheated. As a result, the inside of the channel 64 tends to be promptly sterilized. In order to prevent diffusion of the heat delivered from the heat generator 71E into the space portion 47, it is more effective to use insulating material for the channel 64.

When the heat generator 71E is configured as in the present invention, the inside of the channel 64 is directly heated and, thereby the sterilization can be performed more promptly compared with that in the fourth embodiment to sixth embodiment in which heating of the channel 64 is accelerated by superheating the space portion 47. Furthermore, there is a merit that the heat generator 71E is disposed without the need for changing the current configuration of the endoscope 2E.

Therefore, the present embodiment has an advantage that the sterilization can be performed promptly without changing the configuration of the endoscope 2E in addition to the advantage of the fourth embodiment.

The present invention also includes an embodiment configured by, for example, partially combining each of the above-described third to seventh embodiments.

As described above, according to the third to seventh embodiments, the sterilization of the inside of the channel built in the endoscope can be performed more promptly and reliably. In the cleaning step as well, the cleaning step can be performed without effort while the watertightness of the space portion is maintained.

Eighth Embodiment

Figure 33:
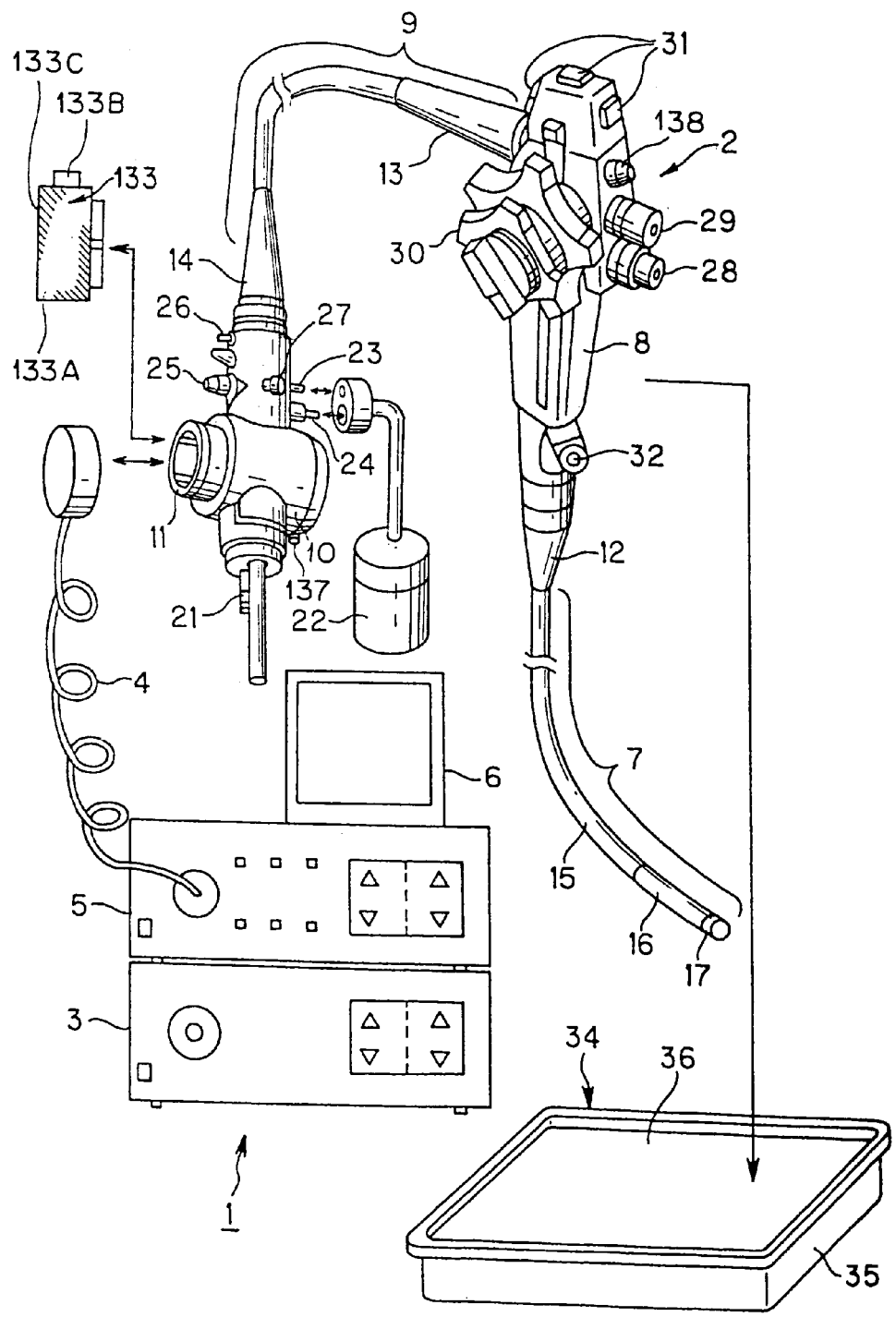
FIG. 33 is a configuration diagram showing the configuration of an entire endoscope system including an endoscope apparatus according to an eighth embodiment of the present invention.
Figure 34:
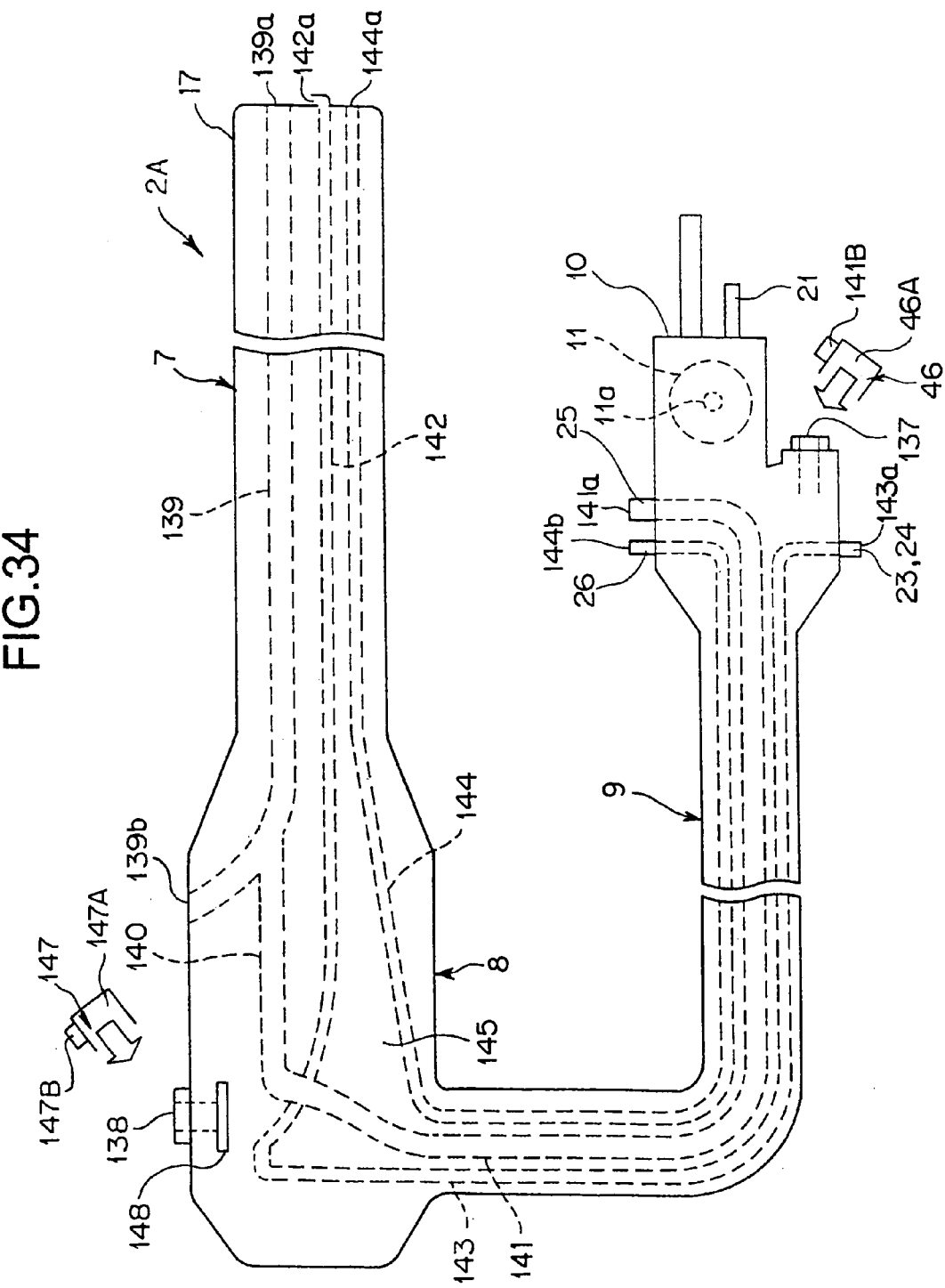
FIG. 34 is a diagram schematically showing a channel system of the endoscope shown in FIG. 33.
Figure 35:
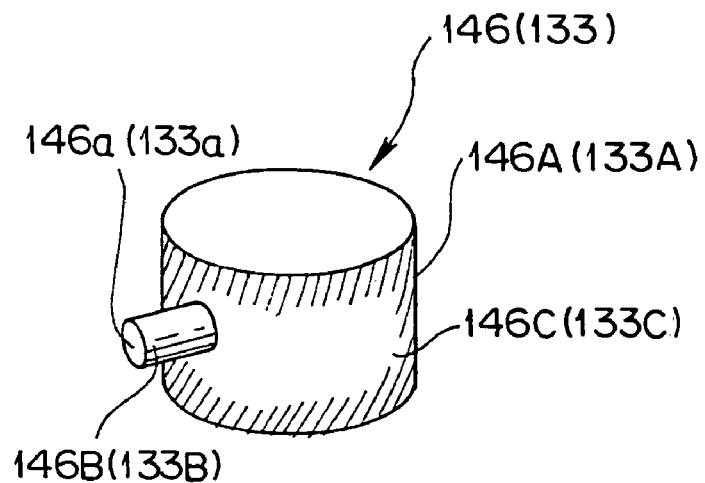
FIG. 35 is a perspective view showing the external configuration of a watertight cap used in the endoscope shown in FIG. 34.
Figure 36:
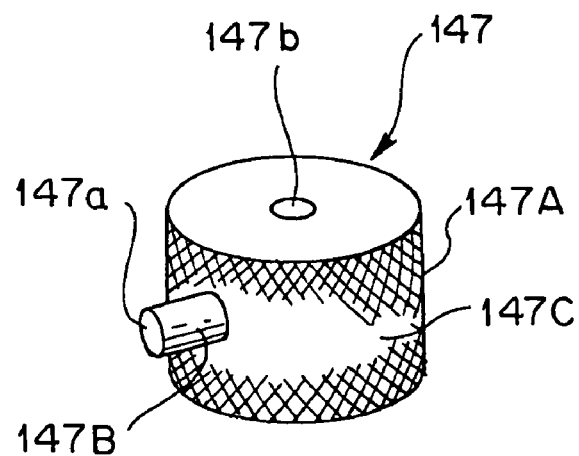
FIG. 36 is a perspective view showing the external configuration of another watertight cap used in the endoscope shown in FIG. 34.

FIG. 33 to FIG. 36 show an endoscope according to an eighth embodiment of the present invention. FIG. 33 is a configuration diagram showing the configuration of an entire endoscope system including an endoscope apparatus. FIG. 34 is a diagram schematically showing a channel system of the endoscope shown in FIG. 33. FIG. 35 and FIG. 36 are perspective views showing the external configurations of two watertight caps used in the endoscope system shown in FIG. 33. FIG. 35 shows a leak test watertight cap having a leak test base, and FIG. 36 shows a steam inlet watertight cap having a clogging-detection check valve, wherein the cap can be attached to the steam inlet.

The same configurations as that in the endoscope system shown in FIG. 1 according to the first embodiment are indicated by the same reference numerals as in the first embodiment, explanations thereof will not be provided, and different points will be primarily described.

In the present embodiment, a vent portion 137 is disposed in the connector portion 10. The vent portion 137 is a communication hole which makes a space portion 145 in a watertightly enclosed region between the outer surfaces of the channels inserted through the inside of the endoscope 2 and the outer covering member (integument portion) of the endoscope 2 (refer to FIG. 34) communicate with the outside of the endoscope.

Furthermore, a vent portion 11a (refer to FIG. 34) which makes the space portion 145 of the endoscope 2 (refer to FIG. 34) communicate with the outside of the endoscope is disposed in the electrical connector portion 11, as in the vent portion 137.

In the description on the present embodiment, the connector portion 10 has a configuration in which two vent portions are disposed to make the space portion 145 of the endoscope 2 communicate with the outside of the endoscope, but may has a configuration in which any one of the vent portions is included alone. Any one of the two vent portions 11a and 137 is used as a communication hole for the leak test.

A leak test watertight cap 133 is detachably connected to the electrical connector portion 11. The watertight cap 133 is provided with a leak test base 133B and a pressure control valve, although not shown in the drawing, as described later. In the configuration in which two vent portions are disposed, a leak test watertight cap 146 having the configuration substantially similar to that in the leak test watertight cap 133 is detachably connected to the vent portion 137 of the connector portion 10 (refer to FIG. 34). The leak test watertight cap 133 (146) has a property of keeping the electrical connector portion 11 (or the vent portion 137 of the connector portion 10) watertight when the leak test watertight cap 133 (146) is connected to the electrical connector portion 11 (or the vent portion 137 of the connector portion 10).

In the endoscope 2 of the present embodiment, a steam inlet 138 is disposed at substantially central portion of the control section 8. The steam inlet 138 is a communication hole which makes the space portion 145 in a watertightly enclosed area between the outer surfaces of the channels inserted through the inside of the endoscope 2 and the outer covering member (integument portion) of the endoscope 2 (refer to FIG. 34) communicate with the outside of the endoscope.

A steam inlet watertight cap 147 is detachably connected to the steam inlet 138 of the control section 8, as described later.

The configurations of the leak test watertight cap 133 (146) and the steam inlet watertight cap 147 will be described later.

FIG. 34 is a diagram schematically showing various channels built in the inside of the endoscope 2.

As shown in FIG. 34, the connector portion 10 of the endoscope 2 of the present embodiment is provided with the vent portion 11a (137) which is a hole or opening serving as a leak test hole making the inside of the endoscope 2 communicate with the outside, as described above. Through the vent portion 11a (137), the outside of the endoscope 2 is made to communicate with the inside space portion 145 enclosed by the integument portion of the endoscope 2. Although not shown in the drawing, a filter provided with a plurality of small holes which pass steam but do not pass objects larger than the steam may be disposed in a part of the vent portion 11a (137).

The connector portion 10 is provided with a water supply tank-pressurizing base 23, an air supply base 24, a suction base 25, and an injection base 26, as shared holes or openings communicating with various channels built in the inside of the endoscope 2. The various channels in the endoscope 2 are made to communicate with the outside of the endoscope 2 through these openings.

In the present embodiment, the steam inlet 138 serving as a hole or an opening making the inside of the endoscope 2 communicate with the outside, as described above, is disposed in the neighborhood of the center of the control section of the endoscope 2. Through the steam inlet 138, the outside of the endoscope 2 communicates with the inside space portion 145 enclosed by the integument portion of the endoscope 2.

In the present embodiment, a filter 148 provided with a plurality of small holes which pass steam but do not pass objects larger than the steam, e.g., dust and a lubricant or the like in the inside of the endoscope, is disposed in a part of the steam inlet 138. The filter 148 is detachably attached to the steam inlet 138 and is exchangeable. The filter 148 is a filter, such as a paper filter used for a sterilization package (not shown in the drawing) to perform the sterilization treatment and the like while covering the container case 34 storing the endoscope 2. The filter 148 is not limited to the paper filter for a sterilization package (not shown), and other filters may be used. The filter 148 may be configured to include a chemical indicator or a biochemical indicator for checking the sterilization effect and, thereby, the sterilization effect may be checked when the sterilization treatment is performed.

In the present embodiment, when the sterilization treatment is performed with high-temperature high-pressure steam, the high-temperature high-pressure steam is flowed into the space portion 145 from the vent portion 11a (137) and the steam inlet 138 and, thereby, the outer side of channels, e.g., the air/water supply channel or the like, communicating with the space portion 145 can be heated with the high-temperature high-pressure steam in a short time. That is, the sterilization effect in the channel is accelerated by heating the outer side of the channel. Furthermore, high-temperature high-pressure steam is flowed into each channel in the endoscope 2 from each of the openings of the above-described water supply tank-pressurizing base 23, the air supply base 24, the suction base 25, and the injection base 26 and, thereby, the inside of each of channels communicating these openings can be heated with the high-temperature high-pressure steam in a short time. In this manner, the inside of the channel built in the endoscope can be promptly subjected to a sterilization treatment by heating the channel from the inside and the outside.

Each of the channels is arranged as shown in FIG. 34.

A channel 139 is primarily included in the insertion portion 7, and a channel front end 139a is opened to the outside at the distal end portion 17. A channel back end 139b is opened to the outside at the control section 8. The channel 139 is a channel serving for inserting a treatment tool or for suctioning, for example.

A channel 141 is primarily included in the connection cord 9, a channel back end 141a thereof is opened to the outside at the connector portion 10 through the suction base 25. The channel 141 is a channel serving for suctioning, for example. A channel 140 is primarily included in the control section 8, the channel front end thereof is shared with the channel front end 139a, and is opened to the outside at the distal end portion 17. The channel back end is shared with the channel back end 141a, and is opened to the outside at the connector portion 10 through the suction base 25.

When the channel back end 141a (suction base 25) is connected to a channel from a suction device, although not shown in the drawing, and suction operation is performed with the suction device while the channel back end 139b is blocked, suction can be performed from the channel front end 139a through the route of the channel 141, the channel 140, and the channel 139.

A channel 142 is primarily included in the insertion portion 7, a channel front end 142a thereof is opened to the outside at the distal end portion 17, and a channel back end 143a is shared with a channel 143 and is opened to the outside at the connector portion 10 through the water supply tank-pressurizing base 23 and the air supply base 24. The channel 142 is an air/water supply channel serving for supplying air or supplying water in cleaning of a lens surface of the distal end portion 17, for example.

The channel 143 is primarily included in the connection cord 9, the channel 143 is shared with a channel front end 142a, and is opened to the outside at the distal end portion 17. The channel back end 143a is opened to the outside at the connector portion 10 through the water supply tank-pressurizing base 23 and the air supply base 24. When air supply or water supply is performed from the channel back end 143a (the water supply tank-pressurizing base 23, the air supply base 24), air supply or water supply can be performed from the channel front end 142a.

A channel 144 is primarily included in the insertion portion 7, the control section 8, and the connection cord 9, a channel front end 144a is opened to the outside at the distal end portion 17, and a channel back end 144b is opened to the outside at the connector portion 10 through the injection base 26. The channel 144 is a channel serving for supplying water frontward to supply a liquid to an observation object, for example.

As described above, in the present embodiment as well, various channels are built in the endoscope 2, while fluids and the like can be inserted through the inside. Furthermore, both the insertion portion 7 and the connection cord 9 are formed from flexible members, and are not solid but hollow. Most of channels in the insertion portion 7 and the connection cord 9 are arranged in a hollow portion while being in an unfixed state in order to meet flexible movement, and the periphery of the channel is substantially space although other built-in members are present.

Outer sides of these channels (and inside of the integument of the endoscope 2) in middle portions of the channels other than end portions communicate with the surrounding space portion 145, and the space portion 145 communicates with the outside through the vent portion 11a (137) and the steam inlet 138. That is, the outer sides of the channels are in the state of communicating with the outside through the vent portion 11a (137) and the steam inlet 138 communicating with the space portion 145. This communication state through the vent portion 11a (137) can be selected by attachment/non-attachment (detachment) of the leak test watertight cap 133. The communication state through the steam inlet 138 can be selected by attachment/non-attachment (detachment) of the steam inlet watertight cap 147.

In the present embodiment, for example, a space for forming the space portion 145 is ensured in the periphery of the middle portion of the path bonding one opening and another opening of some channel without filling the inside of the integument of the endoscope 2 with fillers and solid matters. Although various built-in members and components are present at some midpoints of the path between the space portion 145 and the vent portion 11a (137), these are arranged in order to avoid interfering the flow of the steam. Therefore, the steam can pass through this path without being hindered.

In the endoscope 2 of the present embodiment, since the vent portion 11a (137) and the steam inlet 138 are disposed, and are allowed to communicate with the space portion 145 in the periphery of each channel disposed in the inside of the endoscope 2 when the sterilization treatment is performed, the space portion 145 can also be adjusted to become in the pre-vacuum state during the pre-vacuum. Since channel openings, e.g., the water supply tank-pressurizing base 23, the air supply base 24, the suction base 25, and the injection base 26, are disposed, and are allowed to communicate with each of the channels disposed in the inside of the endoscope 2 when the sterilization treatment is performed, the inside of each channel can also be adjusted to become in the pre-vacuum state during the pre-vacuum. In the case where a leak test (water leakage test) is performed prior to performing the sterilization treatment, the leak test watertight cap 133 (146) is attached to the vent portion 11a (137), the steam inlet watertight cap 147 is attached to the steam inlet 138 and, thereby, the vent portion 11a (137) and the steam inlet 138 can be kept watertight when the leak test and the cleaning treatment are performed.

Consequently, in the following high-temperature high-pressure steam sterilization step of the endoscope 2, the space portion 145 in the outside of the channel as well as the inside of the channel can be supplied and filled in with high-temperature high-pressure steam and, thereby, the high-temperature high-pressure steam sterilization treatment can be completed in a short time.

The configurations of the leak test watertight cap 133 (146) and the steam inlet watertight cap 147 will be described below with reference to FIG. 35.

As shown in FIG. 35, the leak test watertight cap 133 (146) is a conventionally used cap, and includes a watertight cap main body 133A (146A) to keep the vent portion 11a (137) watertight and a leak test base 133B (146B) which is disposed on the side surface of the watertight cap main body 133A (146A) and which is to be connected to a tube from a pressure pump, although not shown in the drawing, during the leak test. The leak test base 133B (146B) has an opening 133a (146a), and the opening 133a (146a) communicates with the vent portion 11a (137) through a pressure control valve (not shown in the drawing) disposed in the inside and the watertight cap main body 133A (146A).

With respect to the leak test watertight cap 133 (146), in the leak test of the endoscope 2, the tube from a pressure pump not shown in the drawing is connected to the leak test base 133B, and the air from the pressure pump is supplied to the inside of the endoscope 2 through the leak test base 133B and the watertight cap main body 133A.

The leak test watertight cap 133 (146) is provided with identification means 133C (146C) which makes the operator possible to distinguish from the steam inlet watertight cap 147. The identification means 133C (146C) is formed by applying a color member, e.g., green, to all around the outer circumference of or a part of the watertight cap main body 133A (146A).

On the other hand, as shown in FIG. 36, the newly disposed steam inlet watertight cap 147 includes a watertight cap main body 147A to keep the steam inlet 138 watertight and a clogging-detection check valve 147B which is disposed on the side surface of the watertight cap main body 147A and which is to determine the presence or absence of clogging in the filter 148 (refer to FIG. 34) during the leak test.

The clogging-detection check valve 147B has an opening 147a, and the opening 147a communicates with the steam inlet 138 through a pressure control valve (not shown in the drawing) disposed in the inside and the watertight cap main body 147A.

The steam inlet watertight cap 147 is provided with identification means 147C which makes the operator possible to distinguish from the leak test watertight cap 133 (146). The identification means 147C is formed by applying a color member, e.g., red, to all around the outer circumference of or a part of the watertight cap main body 147A.

Therefore, the operator can distinguish the leak test watertight cap 133 (146) from the steam inlet watertight cap 147 at first sight by the identification means 133C (146C) and 147C.

In the present embodiment, the identification means are not limited to color members, e.g., green and red. Any method may be used as long as, for example, the operator can identify the types thereof at first sight.

As shown in FIG. 36, the clogging-detection check valve 147B of the steam inlet watertight cap 147 may be disposed on the top surface of the watertight cap main body 147A. In this case, the clogging-detection check valve 147b may be disposed on the top surface of the watertight cap main body 147A, and in addition to this, the clogging-detection check valve 147B may be constructed so as to communicate with the steam inlet 138 and serve as a base for pressurizing to detect clogging in the filter.

The operations of the endoscope system of the present embodiment will be described below with reference to FIG. 33 to FIG. 36.

It is assumed that cleaning is performed after the inspection of the endoscope 2 of the present embodiment.

In this case, the leak test watertight cap 133 (146) is attached to the vent portion 11a (137), and simultaneously, the steam inlet watertight cap 147 is attached to the steam inlet 138. The tube of the pressure pump not shown in the drawing is connected to the leak test base 133B (146B), and the endoscope 2 after inspection is stored in a cleaning apparatus.

In the present embodiment, since the leak test watertight cap 133 (146) and the steam inlet watertight cap 147 are attached, the cleaning liquid and the like do not enter the inside of the endoscope during the cleaning. Since the steam inlet watertight cap 147 is provided with the identification means 147C formed by a color member, e.g., very prominent red or the like, missing the operation of attaching the cap by the operator may be avoided.

Subsequently, the operator performs the leak test of the endoscope 2 under that condition. In this case, the operator can perform the leak test following the same procedure used conventionally and, therefore, the operator can perform the leak test without having an uncomfortable feeling.

Here, in the present embodiment, when the pressure required for the leak test is taken as P1, a maximum set pressure of a leak test apparatus (a pressure pump and the like, although not shown in the drawing) is taken as P2, and the opening pressure of the clogging-detection check valve 147B is taken as P3, the various components are adjusted to satisfy the relationship P1<P3<P2 in the endoscope system of the present embodiment.

Therefore, the operator initially sets the pressure of the leak test apparatus (not shown in the drawing) at the P1, checks that no water leakage is recognized, and changes the set pressure to the pressure P3 or more with no further operation. In this case, if the filter 148 is not clogged, the clogging-detection check valve 147B is opened at this time, so that air is discharged from the opening 147a of the clogging-detection check valve 147B.

On the other hand, if the filter is clogged, air is not adequately supplied to the steam inlet watertight cap 147 and, therefore, this clogging-detection check valve is not opened, so that air is not discharged.

As described above, the operator can perform the leak test and check of the clogging of the filter 148 by substantially the same operation as the conventionally performed operation.

After the leak test, the operator subjects the endoscope 2 to cleaning with a cleaning apparatus while the leak test watertight cap 133 (146) and the steam inlet watertight cap 147 are attached to the endoscope 2. In this case, the operator can perform a cleaning treatment without having any uncomfortable feeling since the treatment is performed as in the conventional cleaning treatment.

After the cleaning treatment, the operator detaches the steam inlet watertight cap 147 from the steam inlet 138 and, thereafter, puts the endoscope 2 into the high-temperature high-pressure steam sterilization apparatus. In this case, the leak test watertight cap 133 (146) may be detached or may not be detached as long as the cap has resistance against the high-temperature high-pressure steam sterilization. Since most of conventional leak test watertight caps have no resistance against the high-temperature high-pressure steam sterilization, it is desirable that the high-temperature high-pressure steam sterilization is performed after the cap is detached. In the present embodiment, the leak test watertight cap 133 (146) and the steam inlet watertight cap 147 are provided with identification means 133C (146C) and 147C which can be distinguished from each other by, for example, color, in order that the operator can readily identify, and the watertight caps are disposed at different locations. Therefore, the operator is prevented from misidentifying the watertight caps.

With respect to the endoscope 2, during the high-temperature high-pressure steam sterilization treatment, steam enters the inside of the endoscope (space portion 145) from the steam inlet 138 (when the leak test watertight cap 133 (146) is detached, from the vent portion 11a (137) as well). Consequently, the outer surfaces and the like of various channels 139 to 144 inserted through the inside of the endoscope 2 can be heated promptly and, thereby, the sterilization in each channel can be performed more promptly than ever. Since the steam inlet 138 is disposed in the neighborhood of the center of the control section 8, steam readily enters the inside of the endoscope (space portion 145). Furthermore, since the outer surface in the periphery of the central portion of the path bonding one opening and another opening of the channel is also heated promptly, the central portion of the channel which has conventionally taken longer time can be subjected to a sterilization treatment promptly.

In the present embodiment, since the filter 148 is disposed in a part of the steam inlet 138, any lubricant or the like do not flows out of the inside of the endoscope during the high-temperature high-pressure steam sterilization treatment. Conversely, any dust or the like do not enter from the outside of the endoscope.

In the present embodiment, since the vent portion 11*a* serving as the leak test hole is a conventionally used leak test hole, the diameter thereof is a very small 1 mm, for example. However, the steam inlet 138 is disposed separately from the vent portion 11*a* and, therefore, the steam inlet 138 may be designed to be of a size adequate for entrance of the steam, for example, to have the diameter of 9 mm.

In the configuration of the present embodiment, when the vent portion 11*a* is disposed as the leak test hole, the vent portion 137 may be used not for the leak test hole, but for a steam inlet. The steam inlet 138 may be disposed in a portion other than the control section 8, if necessary. Alternatively, a plurality of steam inlets may be disposed.

Since the periphery of the electrical connector portion 11 including the vent portion 11*a* as the leak test hole has substantially the same configuration as the conventional configuration, the system, for example, the leak test watertight cap 133, connected to the electrical connector portion 11 is compatible with the conventional system, and fresh component is not necessarily disposed. Therefore, reduction in cost can be expected.

Consequently, according to the configuration of the present embodiment, in addition to the communication hole serving for the leak test, another steam inlet communicating with the inside of the endoscope is disposed and, thereby, sterilization of the inside of the channel built in the endoscope can be performed more promptly than ever.

As described above, the endoscope apparatus of the present embodiment has the configuration in which in addition to the communication hole serving for the leak test, another steam inlet communicating with the inside of the endoscope is disposed and, thereby, there is an advantage that sterilization of the inside of the channel built in the endoscope can be performed more promptly than ever.

The present invention is not limited to the above-described plural embodiments, and various modifications can be made within the scope of the invention.

What is claimed is:

1. A method for autoclave sterilization of an endoscope, comprising the steps of: controlling a space within an endoscope that includes a vent portion to be in communication with an outside of the endoscope, the space defined by an outer side of a channel having at least two channel ends open to the outside and extending through an inside of the endoscope, and an inner side of an outer covering member of the endoscope, so that the space communicates through the vent portion with the outside of the endoscope, and introducing steam into the space via the vent portion, and the outside of the endoscope after the space and the outside of the endoscope are once brought into the negative pressure; and sterilizing the endoscope while the space and the outside of the endoscope are maintained at substantially equal pressures.

2. The method for autoclave sterilization according to claim 1, wherein sterilizing the endoscope includes introducing the steam into the space and the outside of the endoscope, and heating the channel, which communicates with the outside of the endoscope, from the outside and the inside thereof.

3. The method for autoclave sterilization according to claim 1, wherein making the space communicate with the outside comprises to open a communication path, which is disposed in the endoscope and which makes the space communicate with the outside of the endoscope, to the outside of the endoscope.

4. The method for autoclave sterilization according to claim 3, wherein the communication path is closed to the outside of the endoscope during cleaning of the endoscope performed prior to making the space communicate with the outside.

5. The method for autoclave sterilization according to claim 1, wherein bringing into the negative pressure is performed plural times prior to the sterilization while the space and the outside of the endoscope are maintained at substantially equal pressure.

6. The method for autoclave sterilization according to claim 3, wherein the endoscope is stored in a tray prior to the sterilization, while the tray cannot store the endoscope unless the space communicates with the outside of the endoscope through the communication path.

7. The method for autoclave sterilization according to claim 3, wherein the communication path is selectively opened or closed when at least one of the temperature or the pressure becomes at a predetermined condition.

8. An endoscope comprising:
an endoscope body which is covered with an outer covering member includes a channel having at least two ends and extending through an inside of the endoscope body and wherein each end of the first and second channel ends communicate with the outside of the endoscope;
a space portion is formed between an outer surface of the channel and an inner surface of the outer covering member; and
a communication path which communicates with the outside of the endoscope and the space portion for introducing high-temperature high-pressure steam into the space portion to heat the channel from the outer surface;
wherein the communication path comprises a channel member connecting a first end portion, which is opened to the outside of the endoscope at an endoscope part other than an insertion portion, to a second end portion disposed at a predetermined location in the inside of the endoscope, and wherein the introducing of the high-temperature high-pressure steam into the space portion is performed while the space portion and the outside of the endoscope are maintained at substantially equal pressures.

9. An endoscope comprising:
an endoscope body covered by an outer covering member includes a channel having at least two ends extending through an inside of the endoscope, wherein ends of the channel communicate with an outside of the endoscope;
a space portion is formed between the outer surface of the channel and an inner surface of the outer covering member; and
a communication path communicates with the space portion and the outside of the endoscope and serves for introducing high-temperature high-pressure steam into the space portion to heat the channel from the outer surface;
wherein a filter is disposed in the communication path that, passes steam but does not pass objects larger than a predetermined size, and wherein the high-temperature high pressure steam is introduced into the space portion while the space portion and outside of the endoscope are maintained at substantially equal pressures.

10. An endoscope comprising;
an endoscope body including an outer covering member and including a channel having at least two ends, the channel extending through an inside of the endoscope and in communication with an outside of the endoscope;
a space portion is formed by the outer surface of the channel and an inner surface of the outer covering member; and
a plurality of communication paths communicate with the space portion and the outside of the endoscope, wherein at least one of the communication path serve for introducing high-temperature high-pressure steam into the space portion to heat the channel from the outer surface; and at least one communication path serves for a leak test, and wherein the high-temperature high-pressure steam is introduced into the space portion while the space portion and the outside of the endoscope are maintained at substantially equal pressures.

* * * * *